US007429253B2

(12) United States Patent
Shimada et al.

(10) Patent No.: US 7,429,253 B2
(45) Date of Patent: Sep. 30, 2008

(54) WALKING ASSISTANCE SYSTEM

(75) Inventors: Kei Shimada, Wako (JP); Tatsuya Noda, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 220 days.

(21) Appl. No.: 11/230,545

(22) Filed: Sep. 21, 2005

(65) Prior Publication Data

US 2006/0064047 A1 Mar. 23, 2006

(30) Foreign Application Priority Data

Sep. 21, 2004 (JP) ............................ 2004-273319
Sep. 21, 2004 (JP) ............................ 2004-273320
Oct. 20, 2004 (JP) ............................ 2004-305110

(51) Int. Cl.
*A61F 5/00* (2006.01)

(52) U.S. Cl. ............................ 602/16; 602/19; 602/23; 602/26

(58) Field of Classification Search .................... 601/5, 601/16, 19, 23, 26, 34, 35
See application file for complete search history.

(56) References Cited

U.S. PATENT DOCUMENTS

| | | | | |
|---|---|---|---|---|
| 5,961,541 | A * | 10/1999 | Ferrati | 607/49 |
| 6,966,882 | B2 * | 11/2005 | Horst | 601/5 |
| 7,153,242 | B2 * | 12/2006 | Goffer | 482/66 |
| 2004/0158175 | A1 * | 8/2004 | Ikeuchi et al. | 601/5 |

FOREIGN PATENT DOCUMENTS

| | | |
|---|---|---|
| JP | 1-80118 | 5/1989 |
| JP | 2002-301124 A | 10/2002 |

* cited by examiner

*Primary Examiner*—Michael A. Brown
(74) *Attorney, Agent, or Firm*—Birch, Stewart, Kolasch & Birch, LLP

(57) ABSTRACT

A walking assistance system includes an upper leg fitting which is attached along a user's upper leg. The upper leg fitting is formed from an upper leg frame that forms a framework of the upper leg fitting, and an upper leg coupling member that is vertically slidably supported on a guide rail provided on the upper leg frame, rotatably supported around a support shaft, and joined to the upper leg. When the upper leg fitting is made to swing in the fore-and-aft direction relative to the user's hip by a hip joint actuator, the position of the center of swing of the upper end of the upper leg fitting and the position of the hip joint are displaced, but it is possible to make the upper leg coupling member follow the upper leg by moving the upper leg coupling member relative to the upper leg frame, thus eliminating any uncomfortable sensation.

11 Claims, 23 Drawing Sheets

WHEN BENDING LOWER LEG

WHEN BENDING UPPER LEG

WHEN BENDING LOWER LEG

WHEN BENDING UPPER LEG

WALKING ASSISTANCE SYSTEM

CROSS-REFERENCE TO RELATED APPLICATIONS

The present application claims priority under 35 USC 119 to Japanese Patent Application Nos. 2004-273319, filed on Sep. 21, 2004, 2004-273320, filed on Sep. 21, 2004 and 2004-305110, filed on Oct. 20, 2004, the entire contents of which are hereby incorporated by reference.

BACKGROUND OF INVENTION

1. Field of the Invention

The present invention relates to a walking assistance system that assists walking by permitting a user's upper leg swing in the fore-and-aft direction around a hip joint by means of a hip joint actuator and permits a user's lower leg swing in the fore-and-aft direction around a knee joint by means of a knee joint actuator.

The present invention also relates to a walking assistance system that assists walking by permitting a user's lower leg swing in the fore-and-aft direction around a knee joint by means of a knee joint actuator.

2. Description of the Related Art

Japanese Patent Application Laid-open No. 2002-301124 discloses a walking assistance system that assists the movement of a user's upper leg by connecting, via an electric actuator positioned on the outside of the hip joint, a first link fixed to a side face of an abdominal belt wrapped around the user's abdomen and a second link fixed to side faces of upper leg supports wrapped around the user's upper leg, and by making the second link swing in the fore-and-aft direction relative to the first link by means of the electric actuator.

In the walking assistance system having this structure, the upper end of the second link, which is positioned along the user's upper leg, is pivotably supported so that it can swing relative to the hip, and a lower end part thereof is fixed by means of the upper leg supports so that it is unable to move relative to the upper leg.

FIG. 21 of the drawings is a schematic diagram in which the user's upper right leg, equipped with the walking assistance system, is viewed from the front, wherein a point A denotes a pivoting support point of the upper end of the second link of the walking assistance system, a point B denotes a point at which the lower end of the second link is fixed to the upper leg, a point C denotes the user's knee joint, and a point D denotes the user's hip joint. Considering a rectangle ABCD as a four-joint link, a side AD is fixed to the user's hip, a side AB corresponds to the second link, a side CD corresponds to the thighbone, and a side BC corresponds to the upper leg supports.

When a user equipped with the walking assistance system walks, the side BC swings in a direction perpendicular to the paper surface with the point A and the point D as centers, but during this process a slight movement of the side BC in the left-and-right direction within the paper plane is inevitable. In this case, since an angle θ formed between the side AB (the second link 20) and the side BC (the upper leg supports **15*f* and 15*r***) is fixed, in order for the side BC to move in the left-and-right direction within the paper plane, it is necessary for slippage to occur at the point C. That is, the upper leg supports, which are wrapped around the user's upper leg, rub against the upper leg. In this way, when the upper leg supports rub against the upper leg, there is a problem that the skin of the upper leg is pulled, thus giving the user an uncomfortable sensation.

In the walking assistance system disclosed in Japanese Patent Application Laid-open No. 2002-301124, the second link can swing only in the fore-and-aft direction relative to the first link around a left-and-right direction axis, and the user's upper leg can therefore swing only in the fore-and-aft direction.

However, during walking, the upper leg not only swings in the fore-and-aft direction but also swings in the left-and-right direction to a slight extent. Since the above-mentioned conventional arrangement does not have the degree of freedom to allow the upper leg to swing in the left-and-right direction, the user might feel uncomfortable while walking. In order to avoid this, the second link, which is positioned along the upper leg, may be formed from a soft material having flexibility and made to follow the movement of the upper leg in the left-and-right direction, but unless the framework of the walking assistance system including the second link is made to have a certain rigidity, the weight of the walking assistance system itself cannot be let through to the ground, and the weight is imposed on the user, thus putting a large burden on the user.

FIG. 22 of the drawings is a schematic diagram of a knee joint of a human body; reference numeral 01 denotes a thighbone, and reference numeral 02 denotes a shin bone. The upper end of the shin bone 02 is substantially flat, and the lower end of the thighbone 01, which abuts against the shin bone 02, is curved in an arc shape. When, for example, the knee joint is bent in order to sit on a chair, the thighbone 01 swings rearward through 90° relative to the shin bone 02. It is known that during a first stage of the swing the lower end of the thighbone 01 is mainly in rolling contact with the upper end of the shin bone 02, and during a second stage of the swing the lower end of the thighbone 01 is mainly in sliding contact with the upper end of the shin bone 02. Therefore, due to the rolling contact between the shin bone 02 and the thighbone 01 accompanying bending of the knee joint, a lower part of the thighbone moves rearwardly relative to the shin bone 02 by a distance X. Similarly, when, for example, the knee joint is bent in order to kick a lower part of the knee rearwardly, an upper part of the shin bone 02 moves rearwardly relative to the thighbone 01 by a distance X as shown in FIG. 23 of the drawings.

In this way, since in the conventional walking assistance system the upper leg fitting and the lower leg fitting are pivotably supported via the simple pin coupling in spite of the knee joint moving uniquely and in a different manner from a simple pin coupling, the upper leg fitting and the lower leg fitting cannot follow the movement of the knee joint, leading to problem that they rub against the user's skin to provide an uncomfortable sensation.

SUMMARY OF THE INVENTION

The embodiment of the present invention prevents an upper leg coupling member provided in an upper leg frame of an upper leg fitting from rubbing against a user's upper leg, which results in an uncomfortable sensation.

It is another embodiment of the present invention to eliminate the uncomfortable sensation by making the upper leg frame of the upper leg to fit smoothly to follow the movement of the user's upper leg.

It is another embodiment of the present invention to suppress the uncomfortable sensation caused by the upper leg fitting or the lower leg fitting rubbing against the user's skin when the knee joint is bent or stretched.

In an embodiment of the present invention a walking assistance system includes an upper leg fitting attached along a user's upper leg; a lower leg fitting attached along the user's lower leg; a hip joint actuator disposed to one side of the user's hip joint in order to make the upper leg fitting swing in the fore-and-aft direction relative to the user's hip; and a knee joint actuator disposed to one side of the user's knee joint in order to make the lower leg fitting swing in the fore-and-aft direction relative to the upper leg fitting; the upper leg fitting comprising an upper leg frame forming a framework of the upper leg fitting, and an upper leg coupling member provided on the upper leg frame and joined to the upper leg; and the upper leg coupling member being relatively movably supported on the upper leg frame.

With this arrangement, since the upper leg fitting, which is attached along the user's upper leg, is formed from the upper leg frame forming the framework and the upper leg coupling member is supported so that it can move relative to the upper leg frame and is joined to the upper leg, when the upper leg fitting is made to swing in the fore-and-aft direction relative to the user's hip by means of the hip joint actuator, even if it is difficult for the upper leg coupling member to follow the upper leg due to displacement of the position of the center of swing of the upper leg fitting from the position of the hip joint, it is possible to make the upper leg coupling member follow the upper leg smoothly by moving the upper leg coupling member relative to the upper leg frame, thereby eliminating any uncomfortable sensation for the user.

According to an embodiment of the present invention, the upper leg coupling member is supported so that it can slide along the longitudinal direction of the upper leg frame and can rotate around a support shaft extending in the left-and-right direction relative to the upper leg frame.

With this arrangement, since the upper leg coupling member slides along the longitudinal direction of the upper leg frame and rotates around the support shaft extending in the left-and-right direction relative to the upper leg frame, it is possible to make the upper leg coupling member follow the movement of the user's upper leg more smoothly, thus more effectively eliminating any uncomfortable sensation for the user.

According to an embodiment of the present invention, there is provided a walking assistance system including an upper leg fitting attached along a user's upper leg; and a lower leg fitting attached along the user's lower leg with a hip joint actuator disposed to one side of the user's hip joint in order to make the upper leg fitting swing in the fore-and-aft direction relative to the user's hip. A knee joint actuator is disposed to one side of the knee joint in order to make the lower leg fitting swing in the fore-and-aft direction relative to the upper leg fitting. An upper end of an upper leg frame, that forms a framework of the upper leg fitting, is pivotably supported so that it can swing in the left-and-right direction relative to the hip joint actuator around an upper fulcrum pin. The lower end of the upper leg frame is pivotably supported so that it can swing in the left-and-right direction relative to the knee joint actuator around a lower fulcrum pin.

With this arrangement, the upper leg frame forming the framework of the upper leg fitting attached along the user's upper leg is pivotably supported at its upper end so that it can swing in the left-and-right direction around the upper fulcrum pin relative to the hip joint actuator, and is pivotably supported at its lower end so that it can swing in the left-and-right direction around the lower fulcrum pin relative to the knee joint actuator. Therefore, it is possible to permit the upper leg fitting to smoothly follow the movement of the user's upper leg, thus preventing the upper leg fitting from rubbing against the upper leg to eliminate any uncomfortable sensation for the user.

According to an embodiment of the present invention, the length of the upper leg frame is adjustable by an expandable adjustment actuator.

With this arrangement, since the length of the upper leg frame can be adjusted by means of the expandable adjustment actuator, when one walking assistance system is shared among a plurality of users having varied physiques, it is possible to simply adjust the length of the upper leg frame by means of the adjustment actuator, thus enhancing the convenience. Further, even when the user has his or her own walking assistance system, a small displacement caused each time it is attached or detached can be adjusted by the adjustment actuator, thus enhancing the comfort of fit.

According to an embodiment of the present invention, the adjustment actuator has a damper function for damping expansion and contraction of the upper leg frame.

With this arrangement, since the adjustment actuator has a damper function for damping the expansion or contraction of the upper leg frame, an impact imposed on the upper leg frame can be absorbed by the adjustment actuator.

In order to achieve the embodiments of the present invention, there is provided a walking assistance system including an upper leg fitting attached along a user's upper leg; a lower leg fitting attached along the user's lower leg; and a knee joint actuator disposed to one side of the user's knee joint in order to make the upper leg fitting and the lower leg fitting swing relative to each other in the fore-and-aft direction. A housing of the knee joint actuator is provided which is fixed to the lower end of an upper leg frame forming a framework of the upper leg fitting. A rotor of the knee joint actuator is provided which is coupled via a driving force transmission mechanism to the upper end of a lower leg frame forming a framework of the lower leg fitting. The driving force transmission mechanism permits the lower end of the upper leg frame and the upper end of the lower leg frame to move relative to each other in the fore-and-aft direction so as to follow the relative movement in the fore-and-aft direction between the lower end of the upper leg and the upper end of the lower leg accompanying by bending or stretching of the knee joint.

With this arrangement, since the lower end of the upper leg frame fixed to the housing of the knee joint actuator and the upper end of the lower leg frame joined to the rotor of the knee joint actuator via the driving force transmission mechanism are moved relative to each other in the fore-and-aft direction accompanying bending or stretching of the upper leg frame and the lower leg frame, it is possible to make the upper leg fitting and the lower leg fitting follow relative movement in the fore-and-aft direction between the lower end of the upper leg and the upper end of the lower leg accompanying bending and stretching of the knee joint, thereby suppressing any uncomfortable sensation from the upper leg fitting and the lower leg fitting rubbing against the user's skin.

According to an embodiment of the present invention, the driving force transmission mechanism includes an upper leg side gear fixed to the lower end of the upper leg frame, and a lower leg side gear fixed to the upper end of the lower leg frame and meshing with the upper leg side gear. The rotor of the knee joint actuator drives the lower leg side gear so that the lower leg side gear revolves around the upper leg side gear while rotating.

With this arrangement, since the driving force transmission mechanism is formed by meshing the upper leg side gear fixed to the lower end of the upper leg frame with the lower leg side gear fixed to the upper end of the lower leg frame, it is possible to move the upper leg frame and the lower leg frame relative to each other in the fore-and-aft direction to accommodate bending or stretching of the knee joint, by driving the lower leg side gear by means of the rotor of the knee joint actuator so that the lower leg side gear revolves around the upper leg side gear while rotating.

According to an embodiment of the present invention, the driving force transmission mechanism is a planetary gear mechanism including a ring gear fixed to the lower end of the upper leg frame, a sun gear that is fixed to the rotor of the knee joint actuator and that shares a common center with the ring gear, a planetary gear meshing with the sun gear and the ring gear and a planetary carrier that supports the planetary gear so that it can rotate around the sun gear, and that pivotably supports the upper end of the lower leg frame.

With this arrangement, since the driving force transmission mechanism is formed from the ring gear fixed to the lower end of the upper leg frame, the sun gear that is fixed to the rotor of the knee joint actuator and that has a common center with the ring gear, the planetary gear meshing with the sun gear and the ring gear, and the planetary carrier supporting the planetary gear so that it can rotate around the sun gear and pivotably supporting the upper end of the lower leg frame, it is possible to move the upper leg frame and the lower leg frame relative to each other in the fore-and-aft direction to accommodate bending or stretching of the knee joint, by rotating the planetary carrier by means of the rotor of the knee joint actuator so as to move the upper end of the lower leg frame.

According to an embodiment of the present invention, the driving force transmission mechanism is established by fixing the rotor of the knee joint actuator to the upper end of the lower leg frame with a rotating shaft of the rotor of the knee joint actuator positioned lower than the knee joint and the upper end of an upper frame being pivotably supported on the upper leg fitting.

With this arrangement, since the rotating shaft of the rotor of the knee joint actuator is positioned lower than the knee joint, and the upper end of the lower leg frame is pivotably supported on the upper leg fitting, it is possible to absorb relative movement in the fore-and-aft direction between the lower end of the upper leg and the upper end of the lower leg to accommodate bending or stretching of the knee joint by the driving force transmission mechanism which has a simple structure in which the rotor of the knee joint actuator is fixed to the upper end of the lower leg frame.

The above-mentioned objects, other objects, characteristics, and advantages of the present invention will become apparent from an explanation of preferred embodiments that will be described in detail below by reference to the attached drawings.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF PREFERRED EMBODIMENTS

A first embodiment of the present invention is described below by reference to FIG. 1 to FIG. 6.

Figure 1:
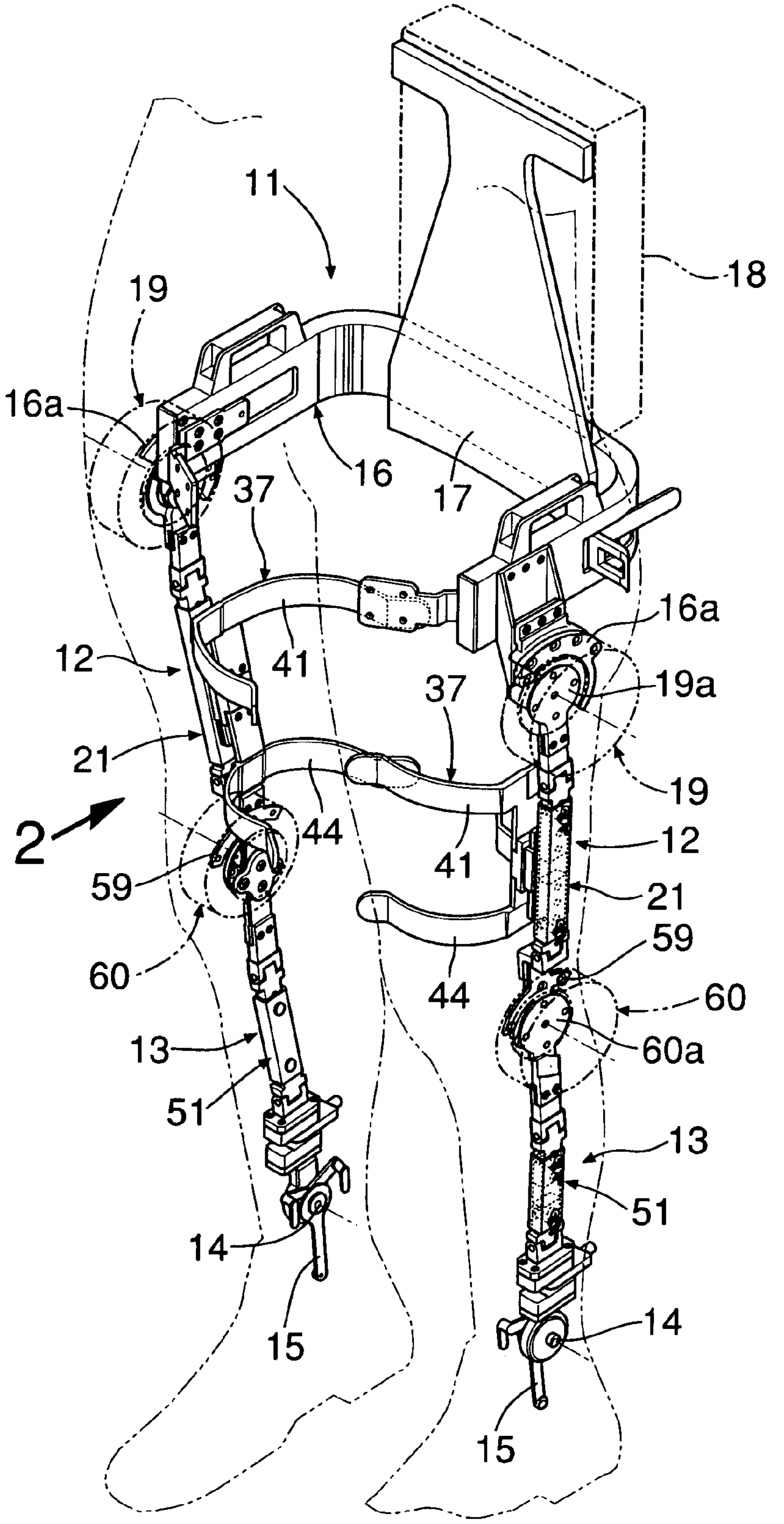
FIG. 1 is an overall perspective view of a walking assistance system.
Figure 2:
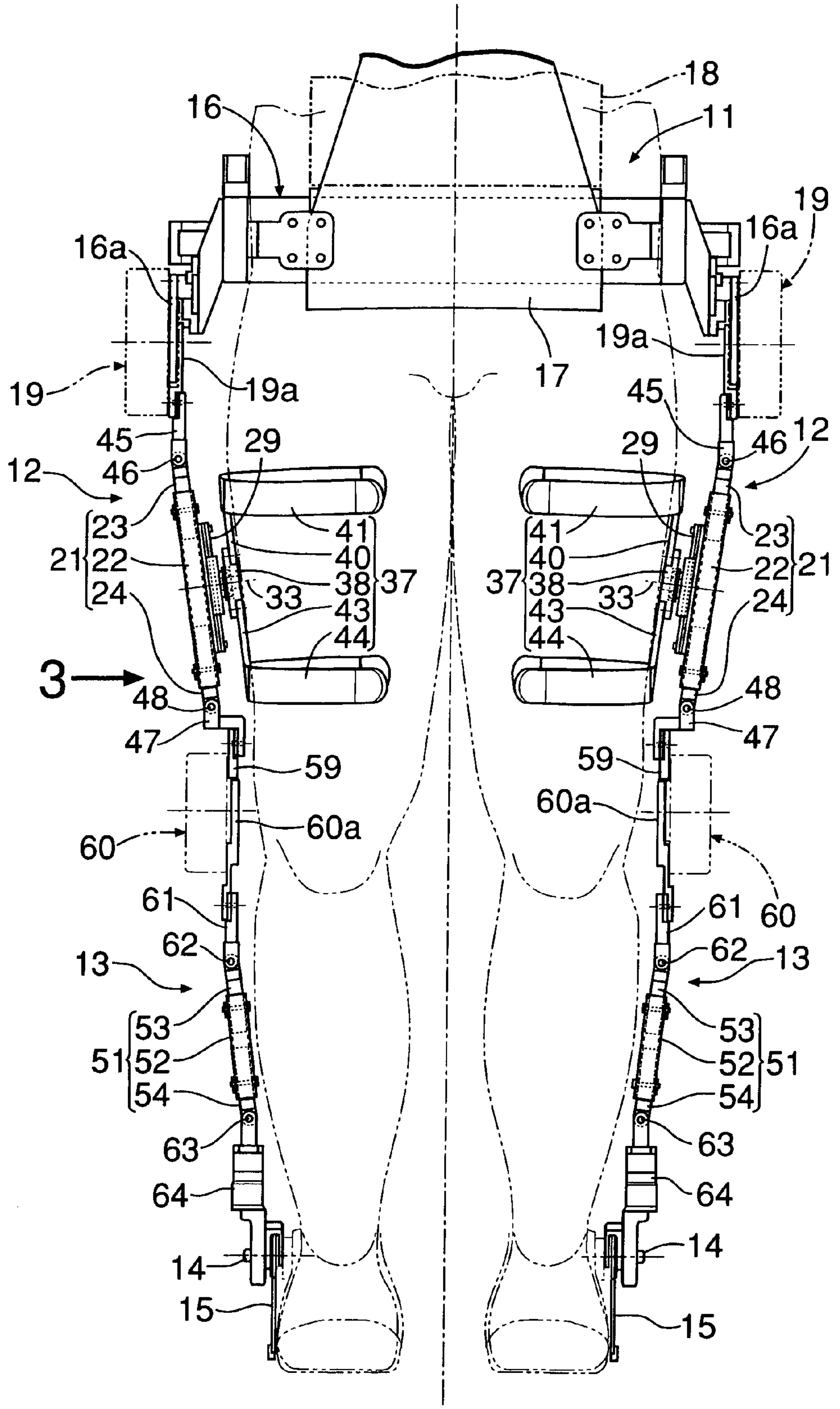
FIG. 2 is a view from arrow 2 in FIG. 1.
Figure 3:
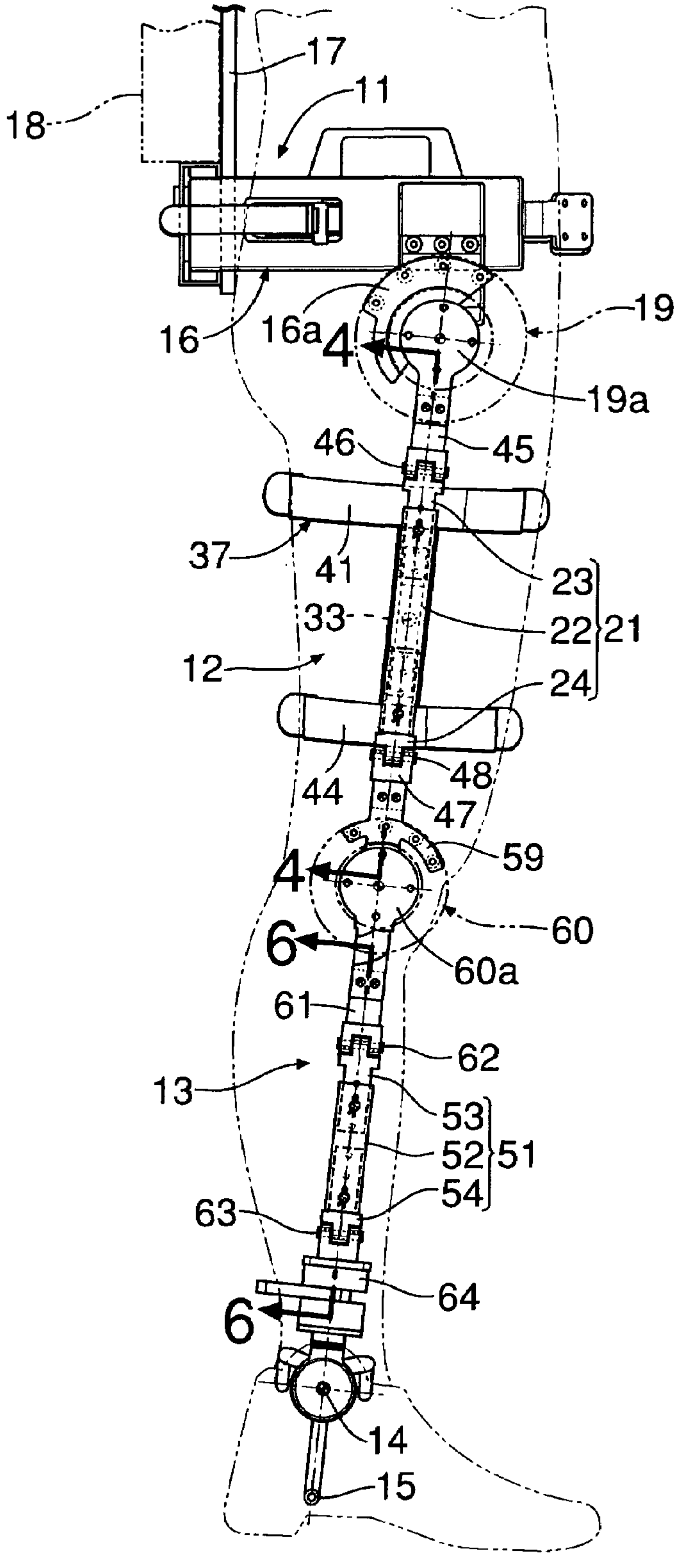
FIG. 3 is a view from arrow 3 in FIG. 2.

As shown in FIG. 1 to FIG. 3, a walking assistance system is attached to a user's left and right legs for assisting walking and is formed from a hip fitting 11 attached so as to surround left and right side parts and a rear part of the user's hip, left and right upper leg fittings 12 pivotably supported at left and right ends of the hip fitting 11 so that they can swing in the fore-and-aft direction and are attached along outer side faces of the user's left and right upper legs. Left and right lower leg fittings 13 are pivotably supported on lower ends of the left and right upper leg fittings 12 so that they can swing in the fore-and-aft direction and are attached along outer side faces of the user's left and right lower legs. Foot frames 15 are pivotably supported at lower ends of the lower leg fittings 13 via fulcrum pins 14 extending in the left-and-right direction so that they can swing in the fore-and-aft direction. The foot frame 15 is fixed to a shoe of the user.

The hip fitting 11 is formed from a U-shaped hip frame 16 that opens toward the front with a back plate 17 that is provided on a rear face of the hip frame 16 and that stands along the user's back. A back pack 18 is supported on a rear face of the back plate 17 with the back pack 18 housing a battery and a control system. Short cylindrical hip joint actuators 19 have their housings fixed to arc-shaped actuator mounting parts 16*a* provided at left and right front ends of the hip frame 16.

Figure 4:
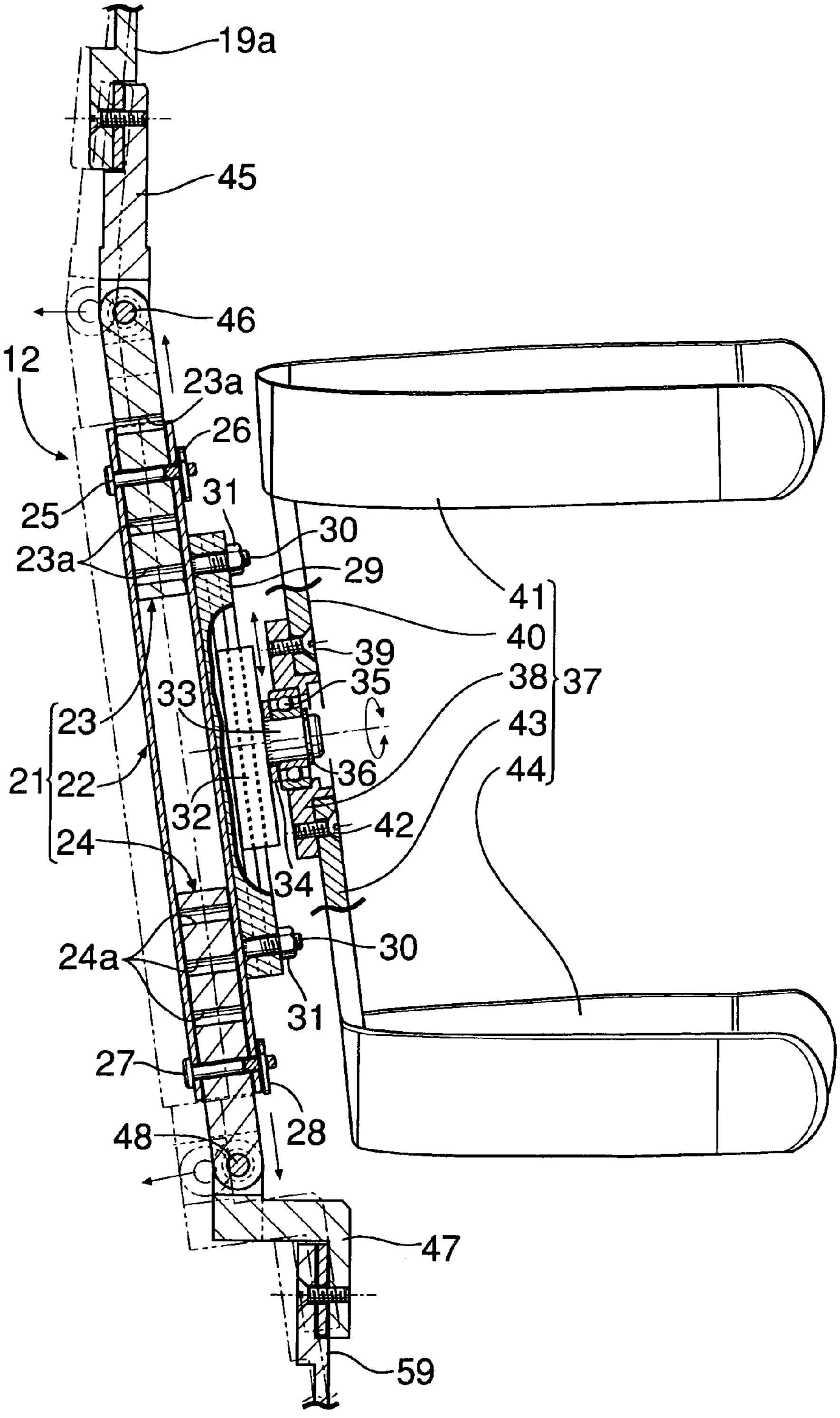
FIG. 4 is an enlarged sectional view along line 4-4 in FIG. 3.
Figure 5:
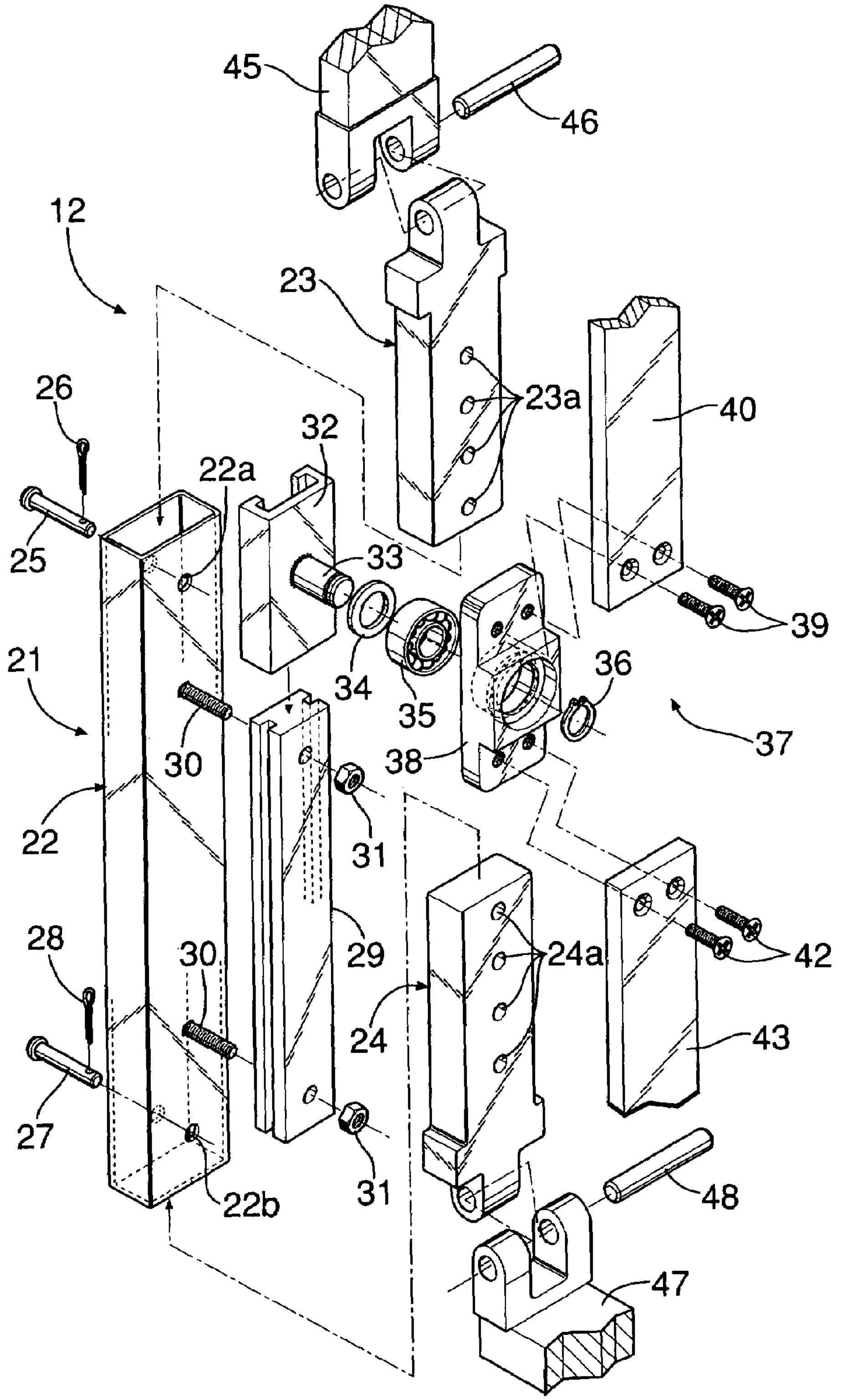
FIG. 5 is an exploded perspective view of an upper leg fitting.
Figure 6:
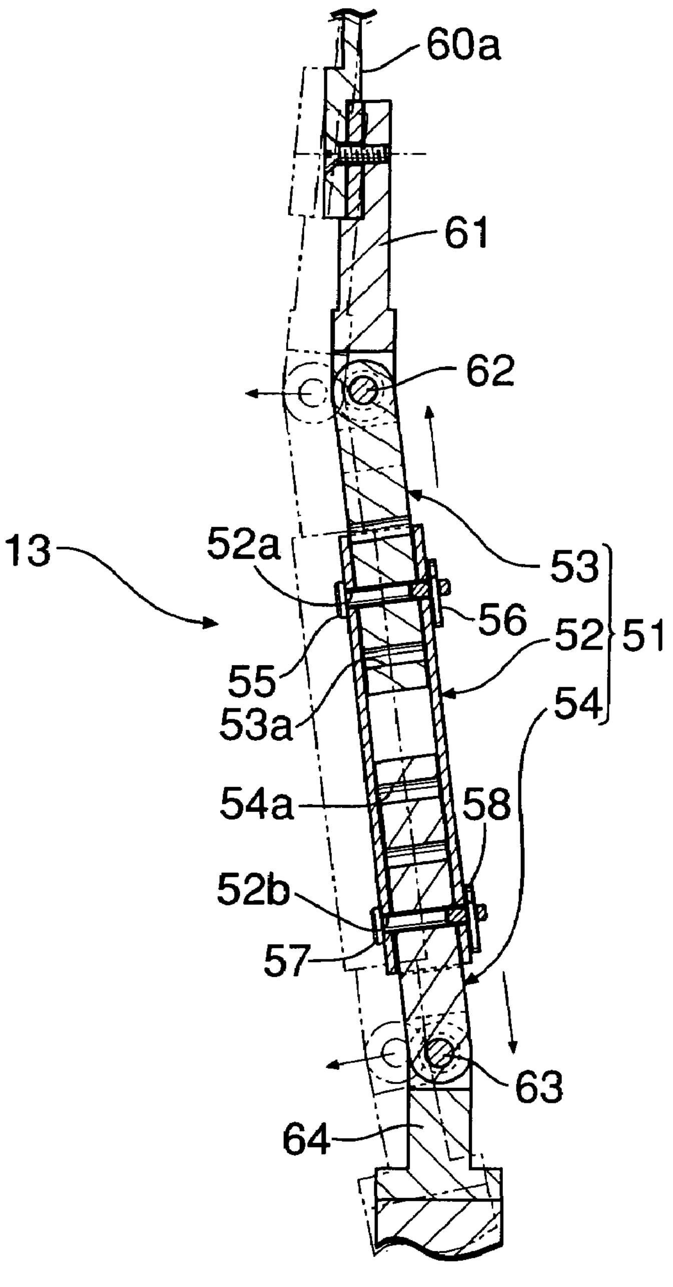
FIG. 6 is an enlarged sectional view along line 6-6 in FIG. 3.

The structure of the upper leg fittings 12 is now described with reference to FIG. 4 and FIG. 5. Since the left and right upper leg fittings 12 have a plane-symmetric structure, the structure of the right upper leg fitting 12 is described as being representative thereof.

An upper leg frame 21 forming the framework of the upper leg fitting 12 is formed from a central frame 22 which is a pipe member having a rectangular cross-section, an upper frame 23 vertically slidably fitted into an inner face of the upper end of the central frame 22, and a lower frame 24 vertically slidably fitted into an inner face of the lower end of the central frame 22. The upper frame 23 and the lower frame 24 are each provided with a plurality (four in this embodiment) of pin holes 23*a* and 24*a*, arranged at predetermined intervals in the vertical direction. Two pin holes 22*a* and 22*b* are provided in an upper part and a lower part of the central frame 22, and are capable of facing the pin holes 23*a* and 24*a*.

Inserting a fixing pin 25 through the pin hole 22*a* on the upper side of the central frame 22 and through any one of the four pin holes 23*a* of the upper frame 23 and preventing the fixing pin 25 from falling out by means of a retaining pin 26, enables the amount of the upper frame 23 projecting upwardly from the central frame 22 to be adjusted in four stages. Inserting a fixing pin 27 through the pin hole 22*b* on the lower side of the central frame 22 and through any one of the four pin holes 24*a* of the lower frame 24 and preventing the fixing pin 27 from falling out by means of a retaining pin 28, enables the amount of the lower frame 24 projecting downwardly from the central frame 22 to be adjusted in four stages.

A guide rail 29 is fixed along an inner face of the central frame 22 by two bolts 30 and two nuts 31, and a slider 32 is fitted slidably onto this guide rail 29. A washer 34 and an inner race of a ball bearing 35 are fitted around a support shaft 33 implanted in the slider 32 and are retained by a clip 36. A rotating member 38 of an upper leg coupling member 37 is press-fitted around an outer race of the ball bearing 35 so that the rotating member 38 can rotate. The upper leg coupling member 37 is formed from a first arm part 40 fixed to an upper part of the rotating member 38 by two bolts 39 so as to face upward, a U-shaped first upper leg coupling part 41 fixed to the upper end of the first arm part 40 and resiliently engaging with a user's upper leg, a second arm part 43 fixed to a lower part of the rotating member 38 by two bolts 42 so as to face downward, and a U-shaped second upper leg coupling part 44 fixed to the lower end of the second arm part 43 and resiliently engaging with the user's upper leg.

The lower end of an output member 45 that is fixed to a rotor 19*a* of a hip joint actuator 19 is bifurcated. The upper end of the upper frame 23 is pivotably supported on the lower end of the output member 45 so that it can swing in the left-and-right direction via an upper fulcrum pin 46 extending in the fore-and-aft direction. The lower end of the lower frame 24 is pivotably supported so that it can swing in the left-and-right direction via a bifurcated upper end part of a coupling member 47 and the lower fulcrum pin 48 extends in the fore-and-aft direction.

The structures of the lower leg fittings 13 are now described by reference to FIG. 1 to FIG. 3 and FIG. 6. Since the left and right lower leg fittings 13 have a plane-symmetric structure, the structure of the right lower leg fitting 13 is described as being representative thereof.

The lower leg fitting 13 has substantially the same structure as that of the upper leg frame 21 of the upper leg fitting 12, and a lower leg frame 51 forming the framework of the lower leg fitting 13 is therefore formed from a central frame 52, which is a pipe member having a rectangular cross-section, an upper frame 53 that is vertically slidably fitted into an inner face of the upper end of the central frame 52, and a lower frame 54 that is vertically slidably fitted into an inner face of the lower end of the central frame 52. The upper frame 53 and the lower frame 54 are each provided with a plurality (three in this embodiment) of pin holes 53*a* and 54*a* arranged at predetermined intervals in the vertical direction. Two pin holes 52*a* and 52*b* are provided in an upper part and a lower part of the central frame 52, the pin holes 52*a* and 52*b* being capable of facing the pin holes 53*a* and 54*a*.

Inserting a fixing pin 55 through the pin hole 52*a* on the upper side of the central frame 52 and through any one of the three pin holes 53*a* of the upper frame 53 and preventing the fixing pin 55 from falling out by means of a retaining pin 56, enables the amount of the upper frame 53 projecting upwardly from the central frame 52 to be adjusted in three stages. Inserting a fixing pin 57 through the pin hole 52*b* on the lower side of the central frame 52 and through any one of the three pin holes 54*a* of the lower frame 54 and preventing the fixing pin 57 from falling out by means of a retaining pin 58, enables the amount of the lower frame 54 projecting downwardly from the central frame 52 to be adjusted in three stages.

A housing of a short cylindrical knee joint actuator 60 is fixed to an arc-shaped actuator mounting bracket 59 fixed to the coupling member 47 positioned at the lower end of the upper leg fitting 12. The upper frame 53 of the lower leg frame 51 is pivotably supported, via an upper fulcrum pin 62 extending in the fore-and-aft direction, at the lower end of an output member 61 fixed to a rotor 60*a* of the knee joint actuator 60 so that it can swing in the left-and-right direction. A coupling member 64 supporting the foot frame 15 via the fulcrum pin 14 is pivotably supported, via a lower fulcrum pin 63 extending in the fore-and-aft direction, at the lower end of the lower frame 54 of the lower leg frame 51 so that it can swing in the left-and-right direction.

The operation of the first embodiment having the above-mentioned arrangement is now described.

While a user is equipped with the walking assistance system, when the hip joint actuators 19 are operated, the left and right upper leg fittings 12 swing alternately in the fore-and-aft direction relative to the hip fitting 11 in a predetermined cycle, and when the knee joint actuators 60 are operated, the left and right lower leg fittings 13 swing alternately in the fore-and-aft direction relative to the upper leg fittings 12 in a predetermined cycle, thus assisting the user to walk.

When the hip joint actuator 19 is operated and the upper leg fitting 12 swings in the fore-and-aft direction relative to the hip fitting 11, since the position of the swing fulcrum at the upper end of the upper leg frame 21 of the upper leg fitting 12 (that is, the rotating shaft of the hip joint actuator 19) and the position of the user's hip joint are displaced in the left-and-right direction, if the upper leg coupling member 37 were fixed to the upper leg frame 21 so that they could not move relative to each other, the upper leg coupling member 37 would rub against the upper leg as the user walks, thus giving the user an uncomfortable sensation.

However, in this embodiment, since the slider 32 supporting the upper leg coupling member 37 is capable of sliding vertically along the guide rail 29 fixed to the upper leg frame 21, and the upper leg coupling member 37 is capable of rotating around the support shaft 33 which is provided on the slider 32 and extends in the left-and-right direction, the displacement in trajectory between the upper leg frame 21 and the user's upper leg can be absorbed by vertical movement and rotation of the upper leg coupling member 37, thus preventing the upper leg coupling member 37 from rubbing against the user's upper leg to eliminate any uncomfortable sensation.

When one walking assistance system is shared among a plurality of users having varied physiques, it is possible to absorb the difference in physique and give a comfortable fit by adjusting the length of the upper leg frames 21 of the upper leg fittings 12. Further, when the walking assistance system is used exclusively by one user, there might be a small displacement of the positions of the hip fitting 11, the upper leg fittings 12, and the lower leg fittings 13 that causes the walking assistance system to not fit the body and gives an uncomfortable sensation. Also, in this case, the uncomfortable sensation can be eliminated by adjusting the length of the upper leg frame 21.

This adjustment can be carried out simply by adjusting the amount of projection of the upper frame 23 from the central frame 22 of the upper leg frame 21, inserting the fixing pin 25 through the pin hole 22*a* in the upper part of the central frame 22 and any one of the four pin holes 23*a* of the upper frame 23 and retaining it by means of the retaining pin 26, and by adjusting the amount of projection of the lower frame 24 from the central frame 22 of the upper leg frame 21, inserting the fixing pin 27 through the pin hole 22*b* in the lower part of the central frame 22 and any one of the four pin holes 24*a* of the lower frame 24 and retaining it by means of the retaining pin 28, that is, in a very simple manner without requiring a cumbersome tightening operation using a bolt.

Furthermore, since the upper end of the upper leg frame 21 is pivotably supported on the output member 45 connected to the hip joint actuator 19 via the upper fulcrum pin 46, and the lower end of the upper leg frame 21 is pivotably supported on the coupling member 47 connected to the knee joint actuator 60 via the lower fulcrum pin 48, it is possible to make the upper leg frame 21 follow the left-and-right movement of the user's upper leg, thus preventing still more effectively the upper leg coupling member 37 from rubbing against the user's upper leg to eliminate any uncomfortable sensation.

In addition, since the lower leg frame 51 of the lower leg fitting 13 has a similar structure to that of the upper leg frame 21 of the upper leg fitting 12 and its length is therefore adjustable, and the lower leg frame 51 can follow left-and-right movement of the user's lower leg by means of the upper fulcrum pin 62 and the lower fulcrum pin 63, its dimensions can easily be adjusted according to the user's physique. Moreover, any uncomfortable sensation for the user can be eliminated.

Figure 7:
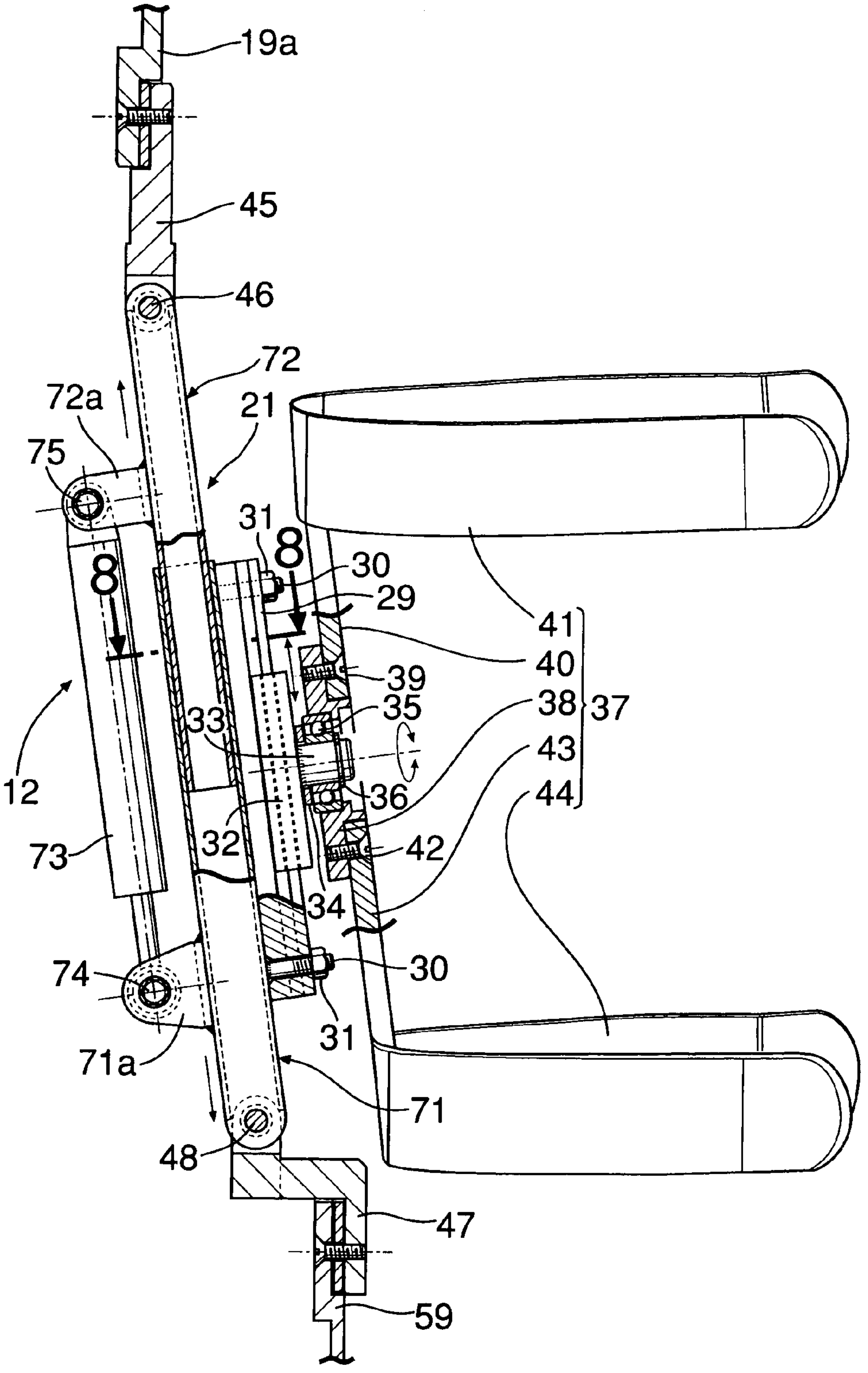
FIG. 7 is a diagram corresponding to FIG. 4.
Figure 8:
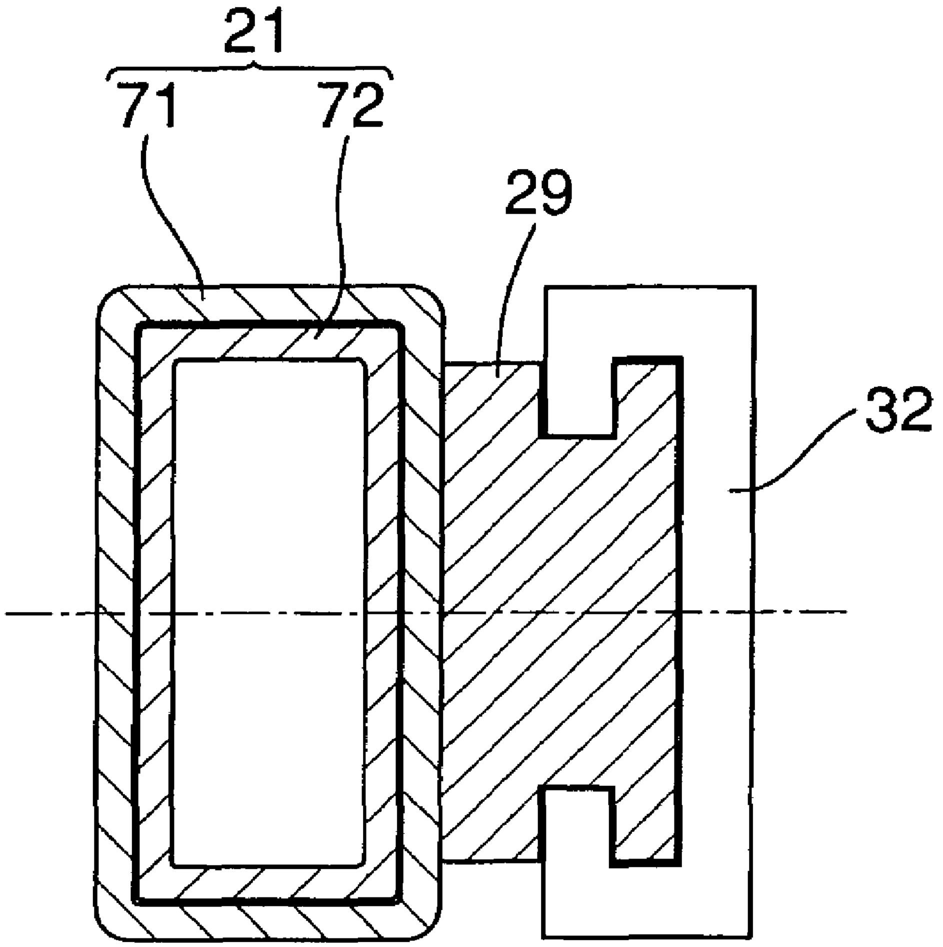
FIG. 8 is an enlarged sectional view along line 8-8 in FIG. 7.

A second embodiment of the present invention is now described by reference to FIG. 7 and FIG. 8.

In the second embodiment, an upper leg fitting 12 has a different structure from that of the first embodiment, but other structures are the same as those of the first embodiment. In an explanation of the second embodiment, members corresponding to the members of the first embodiment are denoted by the same reference numerals and symbols as those of the first embodiment, and duplication of the explanation is therefore omitted.

An upper leg frame 21 of the upper leg fitting 12 of the second embodiment is formed from a lower frame 71 which is a pipe having a rectangular cross-section. An upper frame 72 is slidably fitted into the upper end of the lower frame 71. Opposite ends of a hydraulic cylinder 73 are connected by pins 74 and 75 to a pair of brackets 71*a* and 72*a* that project on side faces of the lower frame 71 and the upper frame 72. When the hydraulic cylinder 73 is expanded or contracted, the amount of projection of the upper frame 72 from the lower frame 71 changes, thus freely adjusting the length of the upper leg frame 21. The hydraulic cylinder 73 has a damper function and generates a damping force against a load that attempts to expand or contract the hydraulic cylinder 73.

A structure in which an upper leg coupling member 37 is rotatably supported via a support shaft 33 on a slider 32 that is engaged slidably with a guide rail 29 fixed to an inner face of the lower frame 71, is the same as that of the first embodiment.

In accordance with this second embodiment, since the length of the upper leg frame 21 can be adjusted freely by expanding or contracting the hydraulic cylinder 73, the adjustment operation is further easily performed. Moreover, since the hydraulic cylinder 73 has the damper function, when a large load is applied to the upper leg frame 21, the hydraulic cylinder 73 contracts to absorb an impact.

The other operational effects of the second embodiment are the same as the above-mentioned operational effects of the first embodiment.

A third embodiment of the present invention is now described by reference to FIG. 9 to FIG. 16B. Members denoted by reference numerals and symbols used in explanations of third to fifth embodiments might be different from members denoted by the same reference numerals and symbols in the above-mentioned first and second embodiments.

Figure 9:
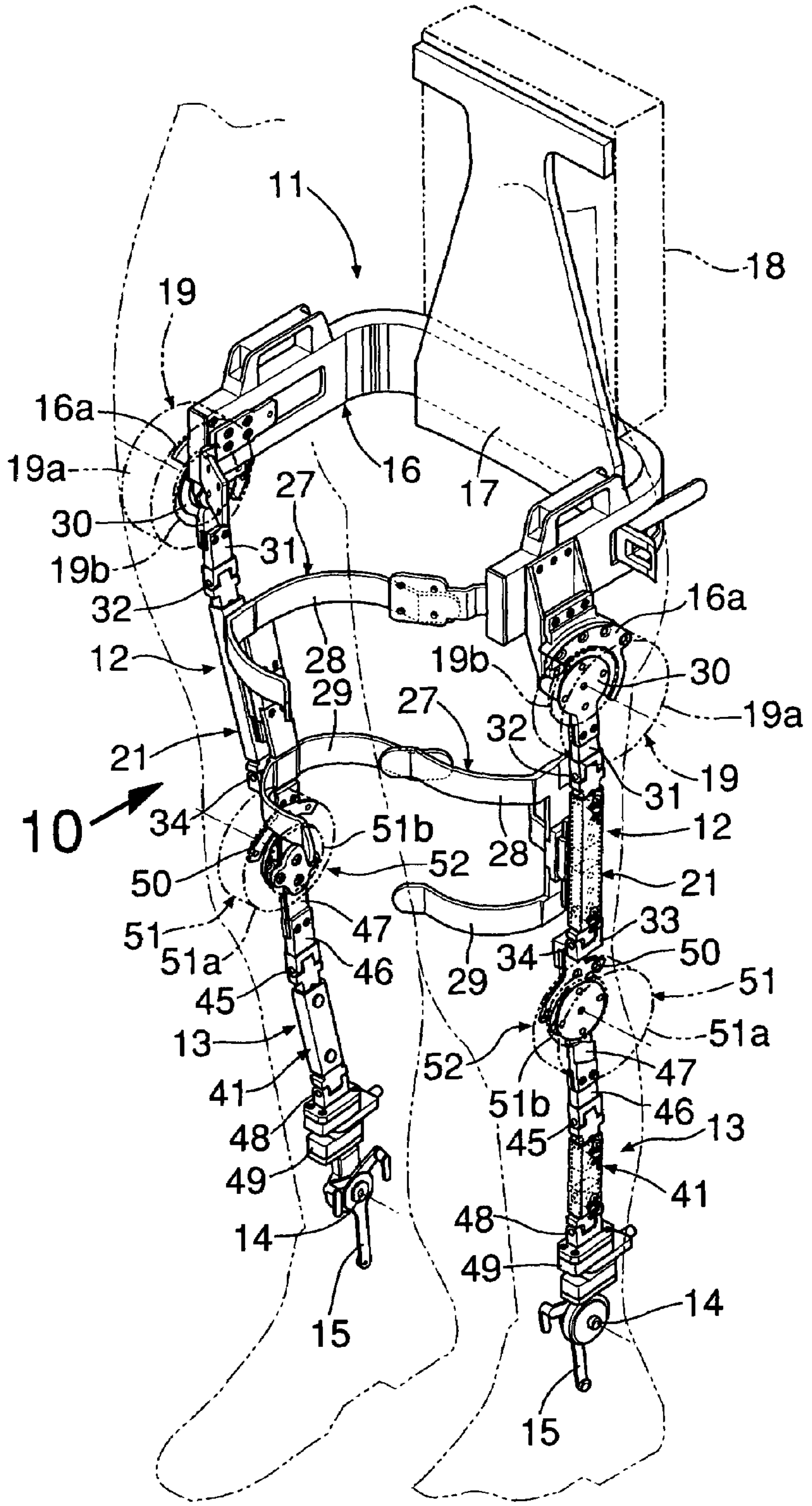
FIG. 9 is an overall perspective view of a walking assistance system.
Figure 10:
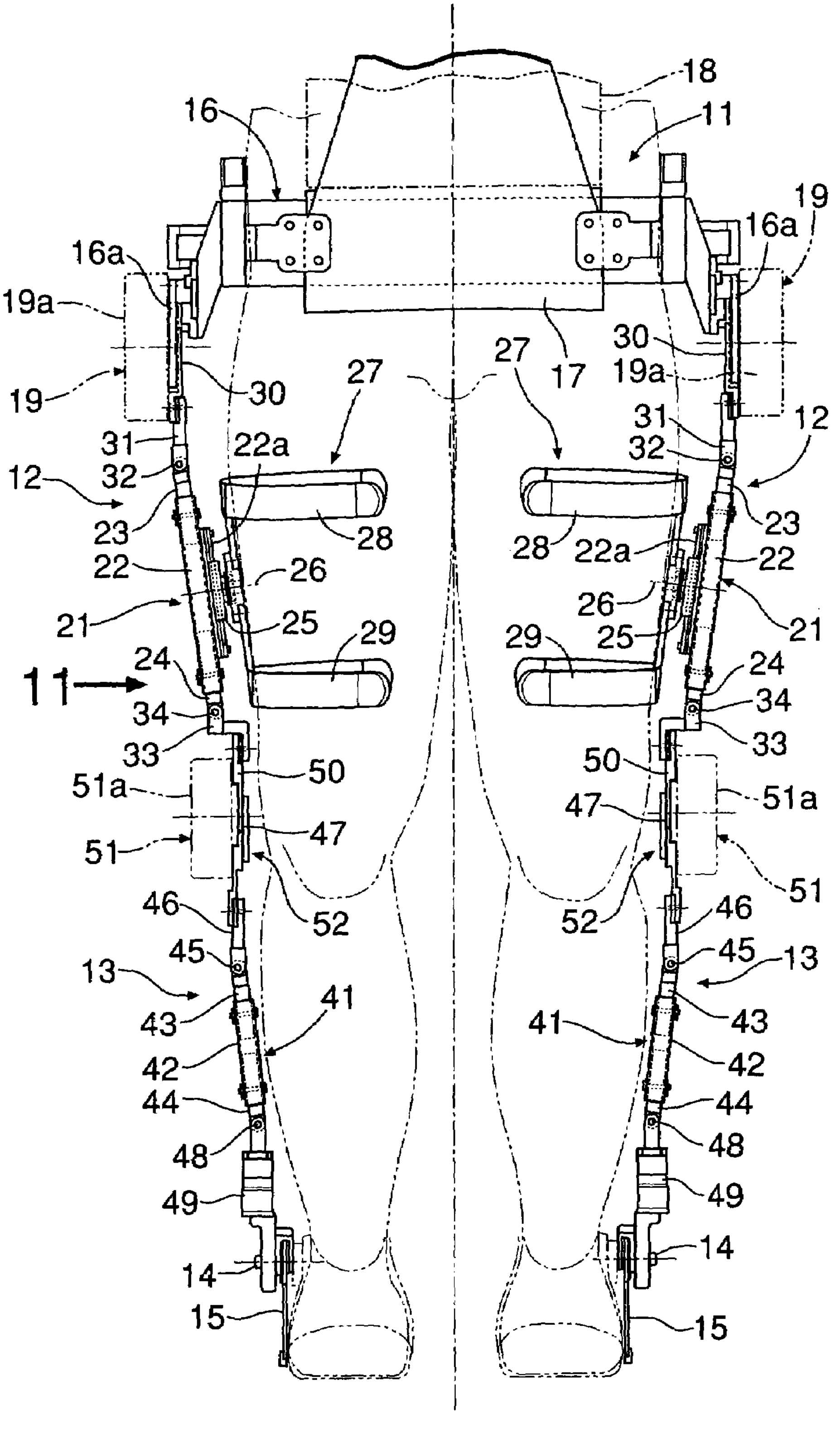
FIG. 10 is a view from arrow 10 in FIG. 9.
Figure 11:
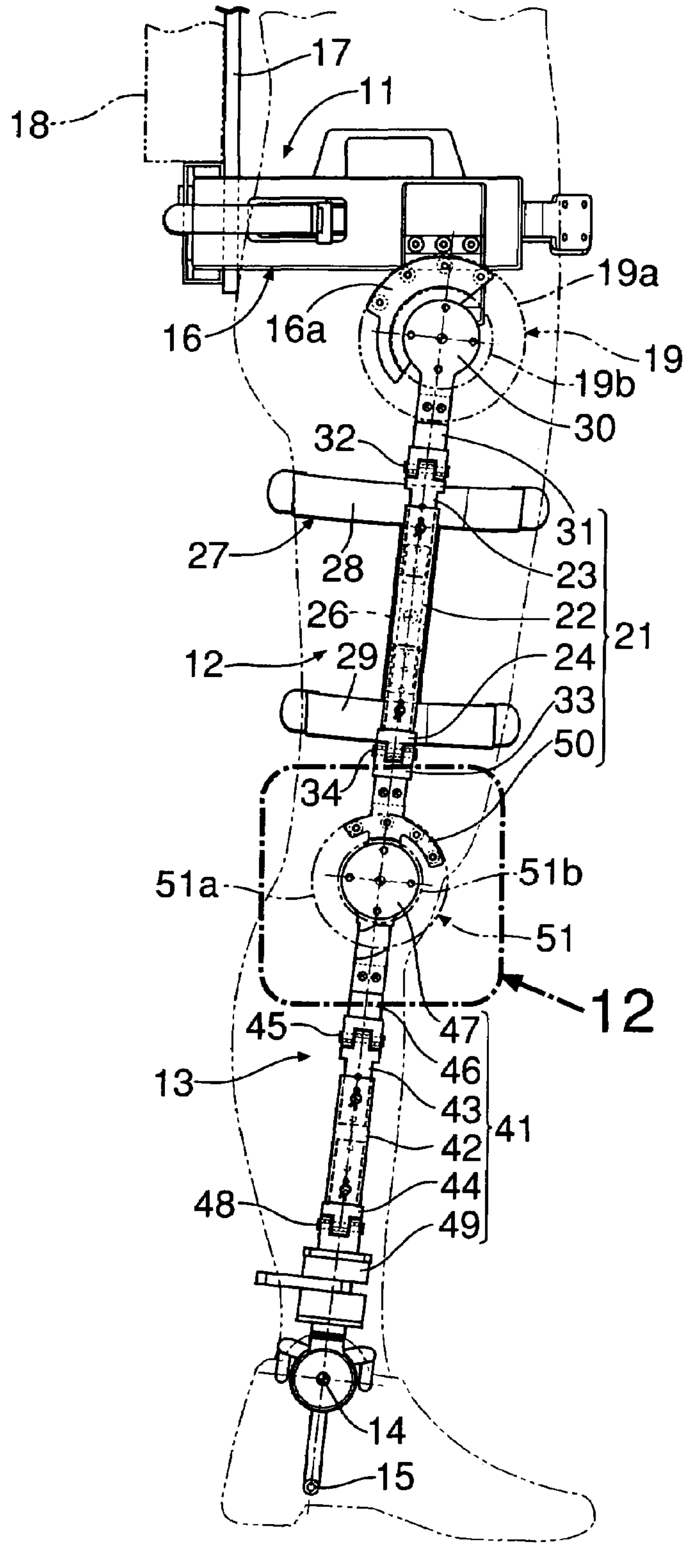
FIG. 11 is a view from arrow 11 in FIG. 10.
Figure 12:
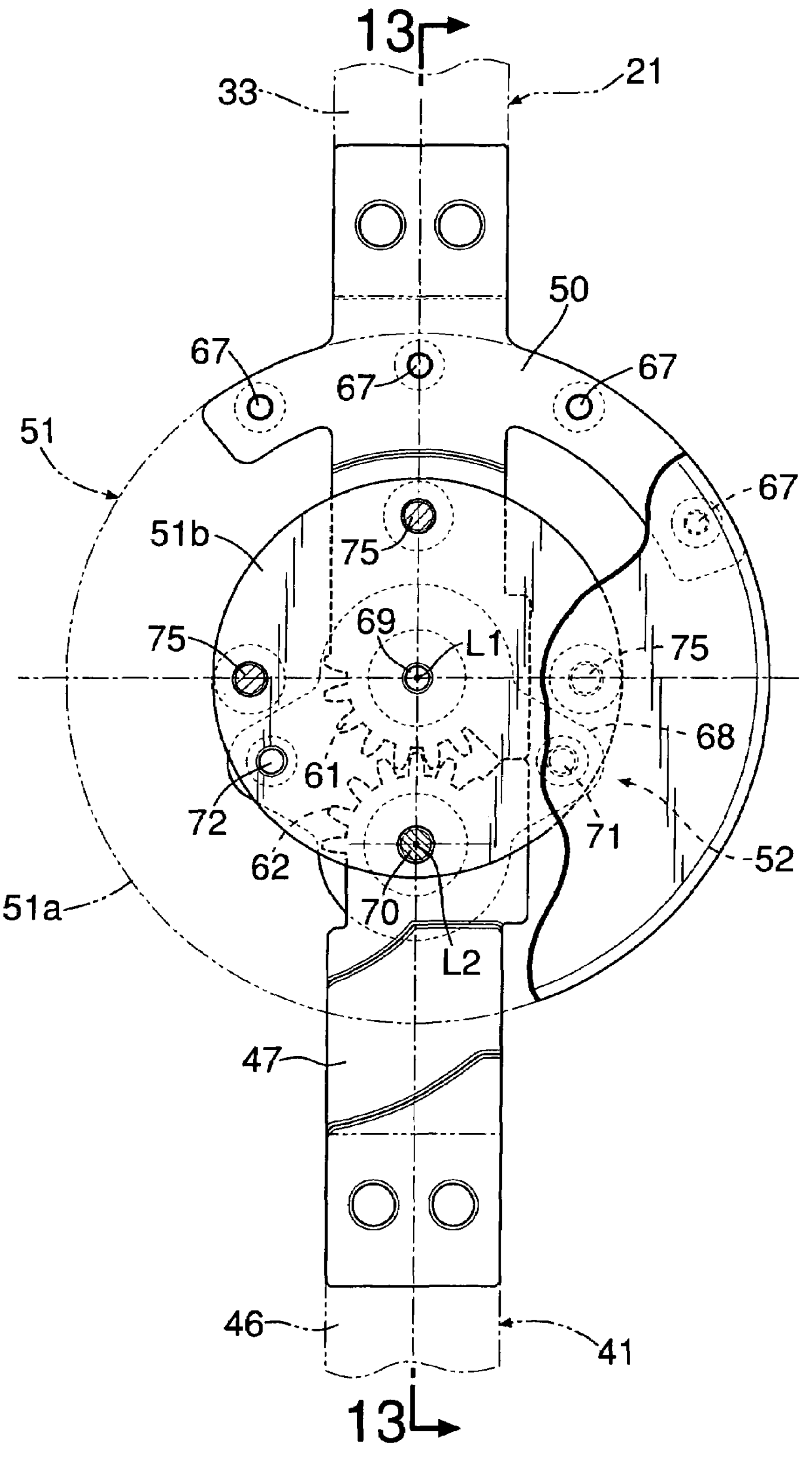
FIG. 12 is an enlarged view of part 12 in FIG. 11.
Figure 13:
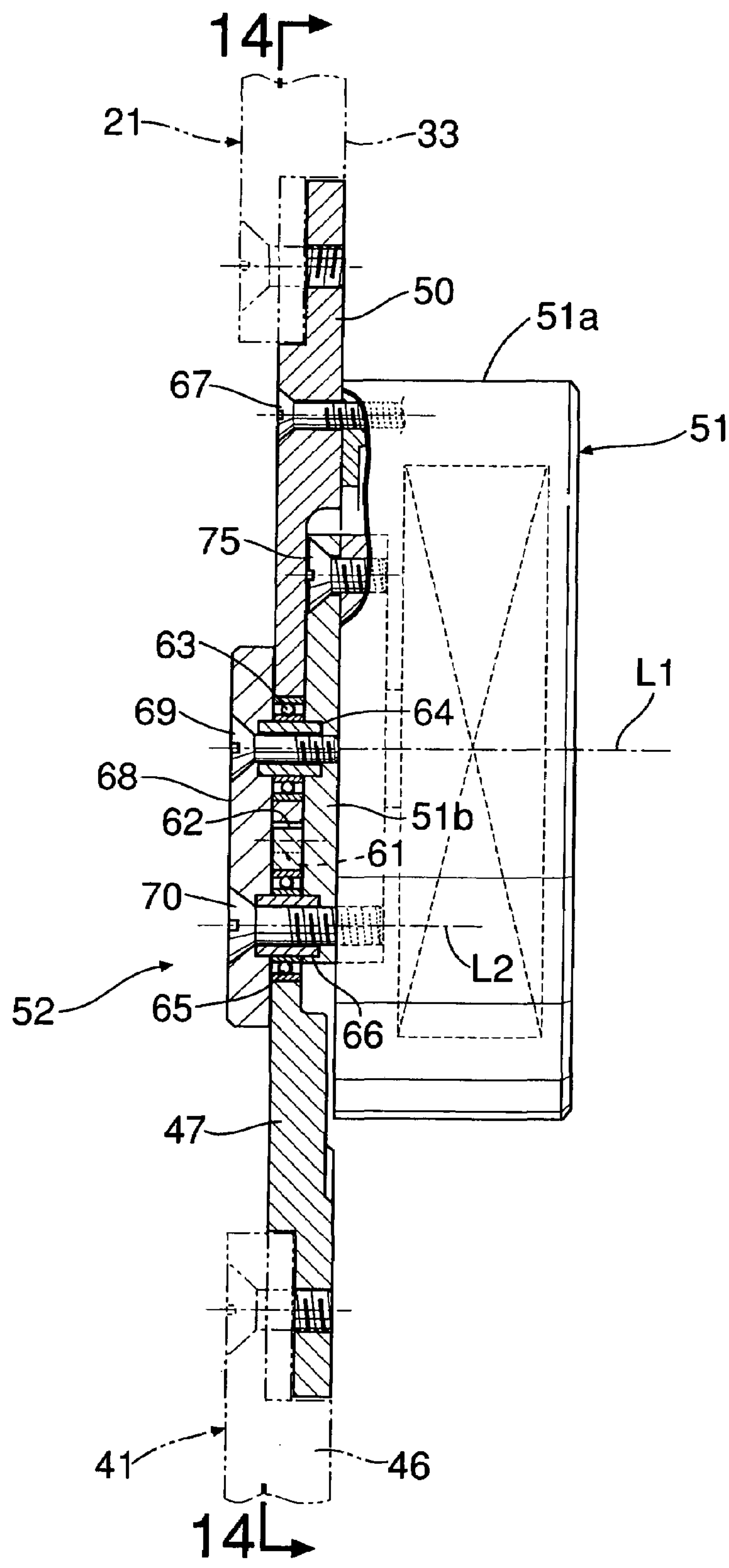
FIG. 13 is a sectional view along line 13-13 in FIG. 12.
Figure 14:
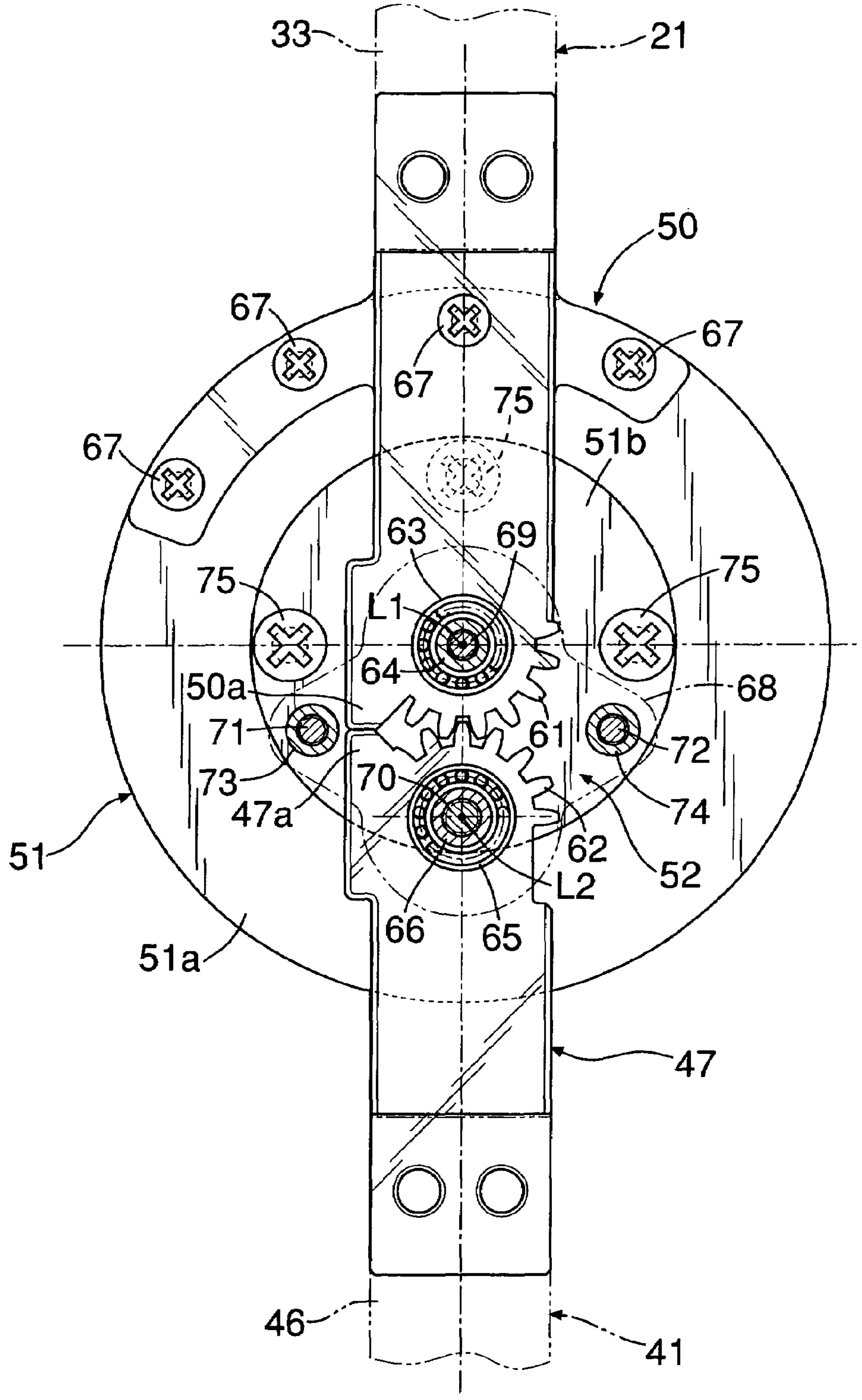
FIG. 14 is a view from arrowed line 14-14 in FIG. 13.
Figure 15:
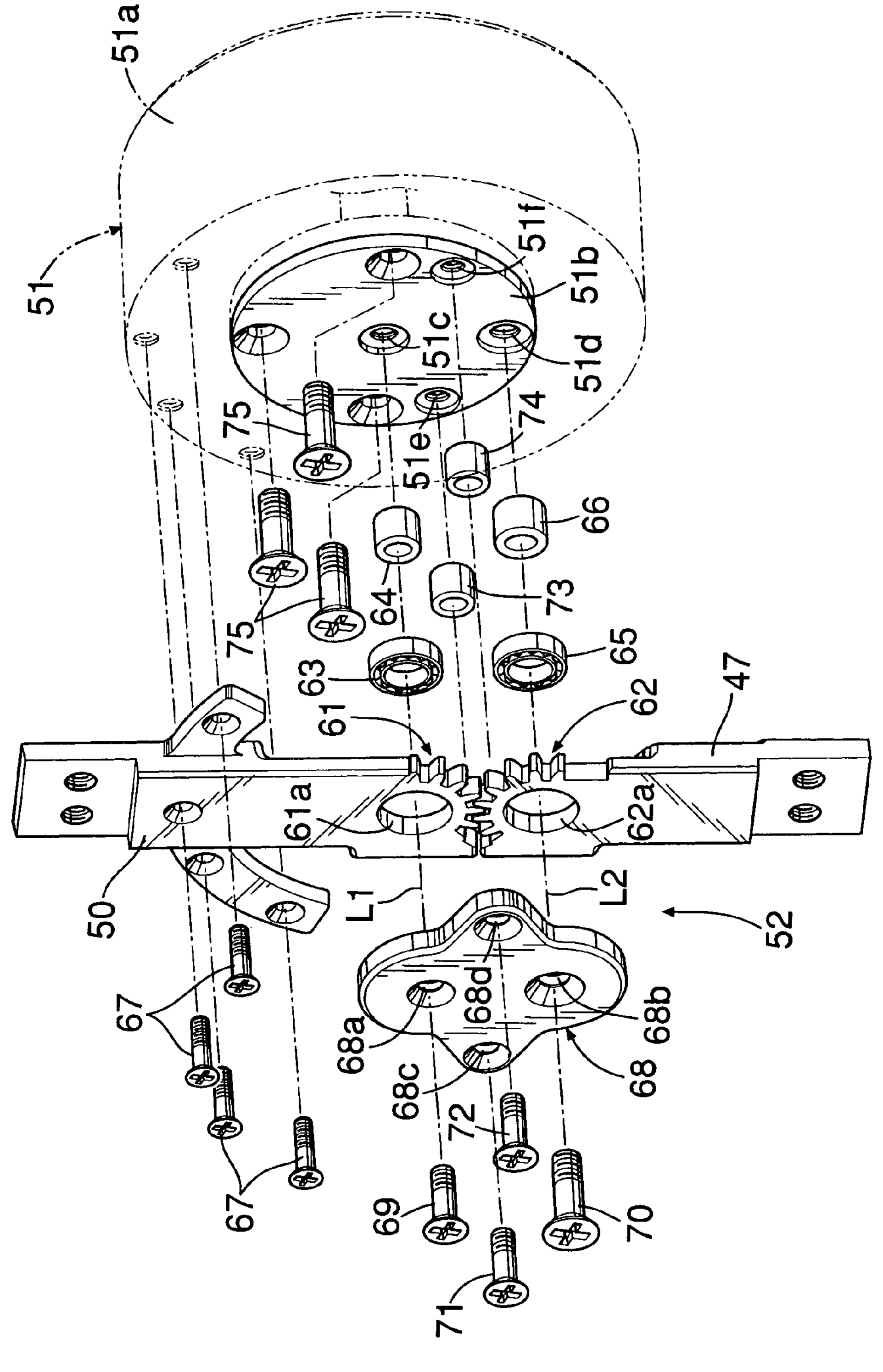
FIG. 15 is an exploded perspective view of a driving force transmission mechanism.

As shown in FIG. 9 to FIG. 11, a walking assistance system is attached to a user's left and right legs for assisting walking and is formed from a hip fitting 11 attached so as to surround left and right side parts and a rear part of the user's hip. Left and right upper leg fittings 12 are pivotably supported at left and right ends of the hip fitting 11 so that they can swing in the fore-and-aft direction and are attached along outer side faces of the user's left and right upper legs. Left and right lower leg fittings 13 are pivotably supported on lower ends of the left and right upper leg fittings 12 so that they can swing in the fore-and-aft direction and are attached along outer side faces of the user's left and right lower legs. Foot frames 15 are pivotably supported via fulcrum pins 14 extending in the left-and-right direction at lower ends of the lower leg fittings 13 so that they can swing in the fore-and-aft direction. The foot frames 15 are fixed to shoes of the user.

The hip fitting 11 is formed from a U-shaped hip frame 16 that opens towards the front, a back plate 17 that is provided on a rear face of the hip frame 16 and that stands along the user's back, and a back pack 18 that is supported on a rear face of the back plate board 17. The back pack 18 houses a battery and a control system. Short cylindrical hip joint actuators 19 have their housings 19*a* fixed to arc-shaped actuator mounting parts 16*a* provided at left and right front ends of the hip frame 16.

An upper leg frame 21 forming the framework of the upper leg fitting 12 is formed from a central frame 22 which is a pipe member having a rectangular cross-section. An upper frame 23 is vertically slidably fitted into an inner face of the upper end of the central frame 22 with a lower frame 24 vertically slidably fitted into an inner face of the lower end of the central frame 22. The length of the upper leg frame 21 can be adjusted according to the user's physique.

An upper leg coupling member 27 is rotatably supported via a support shaft 26 on a slider 25 slidably fitted onto a guide rail 22*a* fixed along an inner face of the central frame 22. The upper leg coupling member 27 includes a U-shaped first upper leg coupling part 28 and second upper leg coupling part 29 which resiliently engage with the user's upper leg.

The lower end of a coupling member 31, connected to a rotor 19*b* of a hip joint actuator 19 via an output member 30, is bifurcated. The upper end of the upper frame 23 is pivotably supported, via an upper fulcrum pin 32 extending in the fore-and-aft direction, on the lower end of the coupling member 31 so that it can swing in the left-and-right direction. The lower end of the lower frame 24 is pivotably supported so that it can swing in the left-and-right direction via the upper end of the coupling member 33 and a lower fulcrum pin 34 extending in the fore-and-aft direction.

The lower leg frame 41 forming the framework of the lower leg fitting 13 has substantially the same structure as that of the upper leg frame 21 of the upper leg fitting 12, and is formed from a central frame 42, which is a pipe member having a rectangular cross-section. An upper frame 43 is vertically slidably fitted into an inner face of the upper end of the central frame 42, and a lower frame 44 is vertically slidably fitted into an inner face of the lower end of the central frame 42. Thus, the length of the lower leg frame 41 can be adjusted according to the user's physique. A coupling member 46 is pivotably supported at the upper end of the upper frame 43 via an upper fulcrum pin 45 extending in the fore-and-aft direction, and an output member 47 is fixed to the upper end of the coupling member 46. A coupling member 49, supporting the foot frame 15, is pivotably supported, via a lower fulcrum pin 48 extending in the fore-and-aft direction, on the lower end of the lower frame 54 of the lower leg frame 41 so that it can swing in the left-and-right direction.

A housing 51*a* of a short cylindrical knee joint actuator 51 is fixed to an actuator mounting bracket 50 fixed to the coupling member 33. A rotor 51*b* of the knee joint actuator 51 is connected to the output member 47 of the lower leg frame 41 via a driving force transmission mechanism 52 which will be described later.

As is clear from FIG. 11, the upper leg frame 21 is formed from the central frame 22, the upper frame 23, the lower frame 24, the coupling member 31, the coupling member 33, and the actuator mounting bracket 50. The lower leg frame 41 is formed from the central frame 42, the upper frame 43, the lower frame 44, the coupling member 46, the output member 47, and the coupling member 49.

The structure of the driving force transmission mechanism 52 for transmitting the driving force of the rotor 51*b* of the knee joint actuator 51 to the lower leg fitting 13 is now described by reference to FIG. 12 to FIG. 16B.

An upper leg side gear 61, which is a sector gear formed at the lower end of the actuator mounting bracket 50 that is a member at the lowermost end of the upper leg frame 21, meshes with a lower leg side gear 62 which is a sector gear formed at the upper end of the output member 47 that is a member at the uppermost end of the lower leg frame 41. An outer race of a ball bearing 63 is fitted into a bearing support hole 61*a* formed in the center of the upper leg side gear 61, and a collar 64 is fitted into an inner race thereof. Similarly, an outer race of a ball bearing 65 is fitted into a bearing support hole 62*a* formed in the center of the lower leg side gear 62, and a collar 66 is fitted into an inner race thereof. The rotor 51*b* of the knee joint actuator 51 which has the housing 51*a* fixed to the actuator mounting bracket 50 by bolts 67, is disposed so that an axis L1 of the rotating shaft of the rotor 51*b* coincides with the center of the upper leg side gear 61.

A stopper 50*a* provided at the lower end of the actuator mounting bracket 50 faces a stopper 47*a* provided at the upper end of the output member 47 so that they can abut against each other. When the upper leg frame 21 and the lower leg frame 41 extend linearly, that is, when the knee joint is stretched, the two stoppers 50*a* and 47*a* abut against each other, thereby preventing the lower leg frame 41 from bending forward relative to the upper leg frame 21.

A connecting plate 68 for maintaining the positional relationship between the upper leg side gear 61 and the lower leg side gear 62 includes four bolt holes 68*a* to 68*d*. A bolt 69 is positioned through the bolt hole 68*a* of the connecting plate 68 and through the ball bearing 63 and the collar 64 and is tightened to a bolt hole 51*c* of the rotor 51*b*. A bolt 70 is positioned through the bolt hole 68*b* of the connecting plate 68 and through the ball bearing 65 and the collar 66 and is tightened into a bolt hole 51*d* of the rotor 51*b*. Two bolts 71 and 72 are positioned through two collars 73 and 74, and are tightened into bolt holes 51*e* and 51*f* of the rotor 51*b*, respectively.

The rotor 51*b* is fixed to a rotating section within the knee joint actuator 51 by the bolt 70 and three bolts 75 are disposed at intervals of 90° relative to the bolt 70.

The operation of the third embodiment having the above-mentioned arrangement is now described.

While a user is equipped with the walking assistance system when the hip joint actuators 19 are operated, the left and right upper leg fittings 12 swing alternately in the fore-and-aft direction relative to the hip fitting 11 in a predetermined cycle. When the knee joint actuators 51 are operated, the left and right lower leg fittings 13 swing alternately in the fore-and-aft direction relative to the upper leg fittings 12 in a predetermined cycle, thus assisting the user to walk.

When the lower leg is kicked up towards the rear relative to the upper leg by bending the knee joint by means of the knee joint actuator 51 and the driving force transmission mechanism 52, if the knee joint actuator 51 fixed to the upper leg frame 21 so as to rotate the rotor 51*b* is driven, the center L2 of the lower leg side gear 62 moves in an arc shape around the center of the upper leg side gear 61 (that is, the axis L1 of the rotor 51*b*) by means of the bolt 70 screwed into the rotor 51*b*.

Figure 16A:
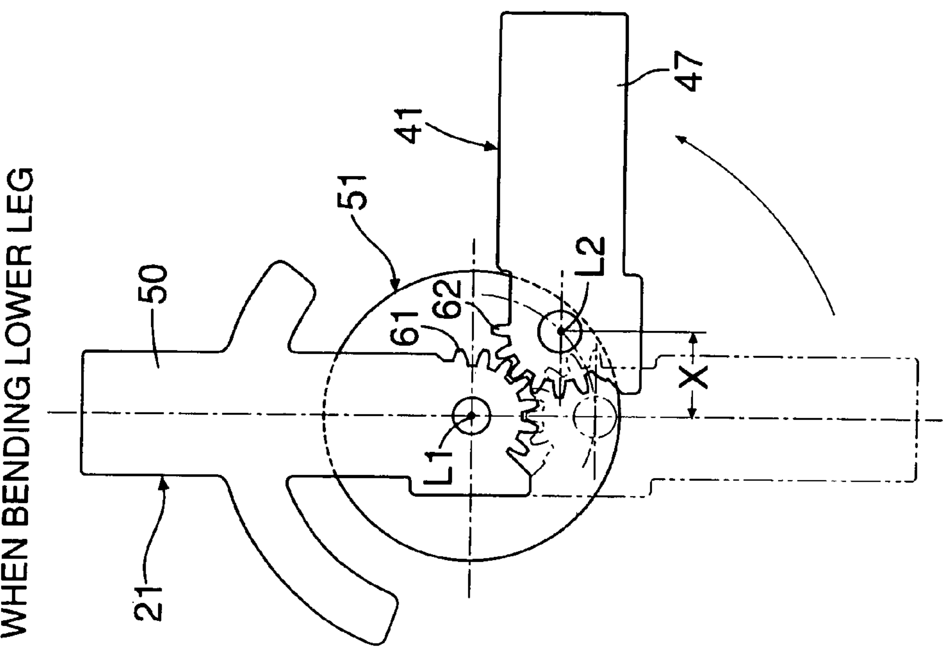
FIG. 16A and FIG. 16B are diagrams for explaining the operation.
Figure 23:
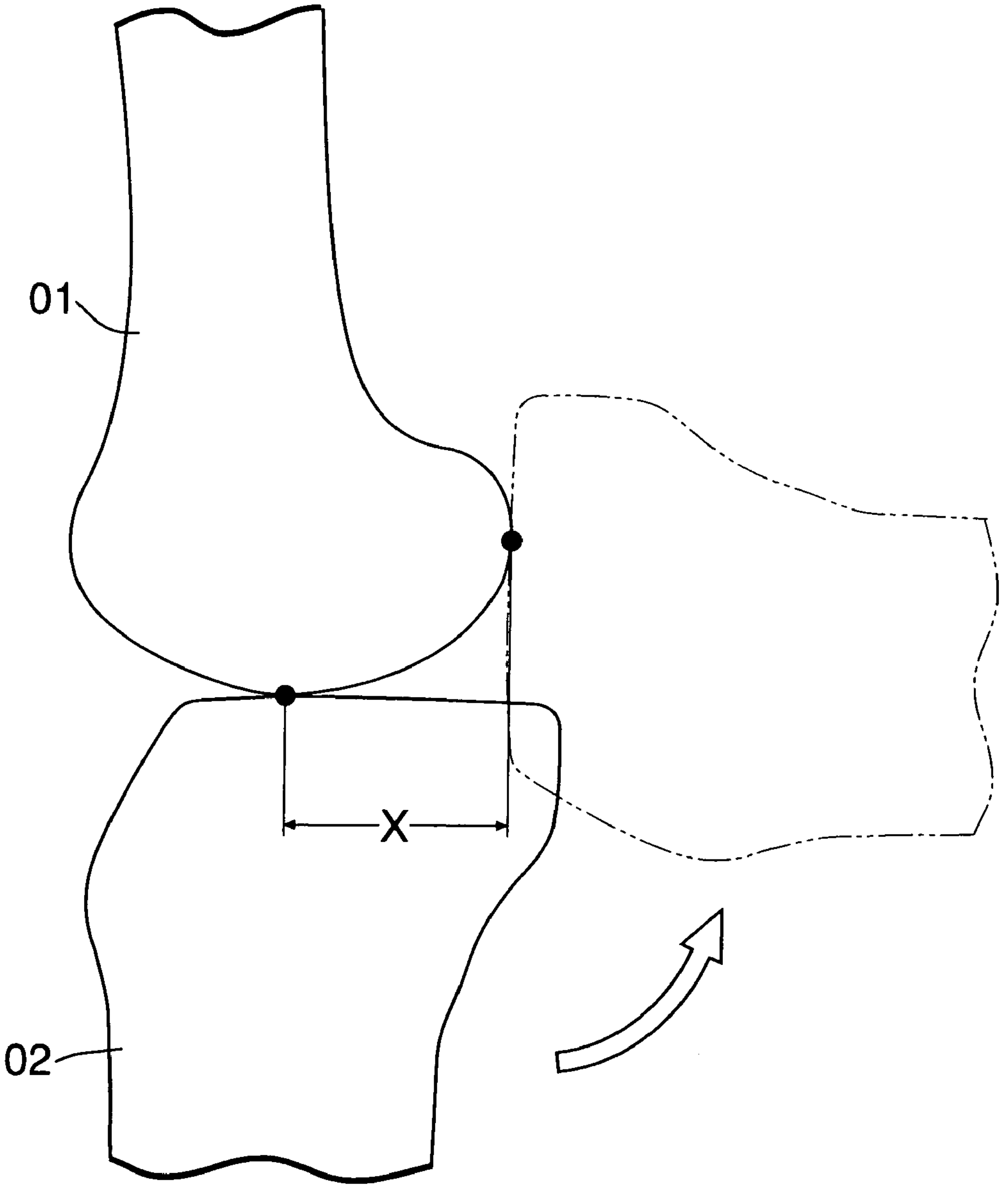
FIG. 23 is a diagram showing a state in which a shin bone is swung rearward relative to a thighbone.

During this process, since the center L2 of the lower leg side gear 62, which meshes with the fixed upper leg side gear 61, moves around an axis L1, the lower leg frame 41 swings rearwardly through 90° relative to the upper leg frame 21 from the broken line position to the solid line position as shown in FIG. 16A and since the position of the center L2 of the lower leg side gear 62 moves rearwardly by a distance X, the displacement X caused when the knee joint is bent as shown in FIG. 23 can be absorbed. This enables the upper leg fitting 12 and the lower leg fitting 13 to be prevented from rubbing against the user's skin, thus suppressing any uncomfortable sensation.

Figure 16B:
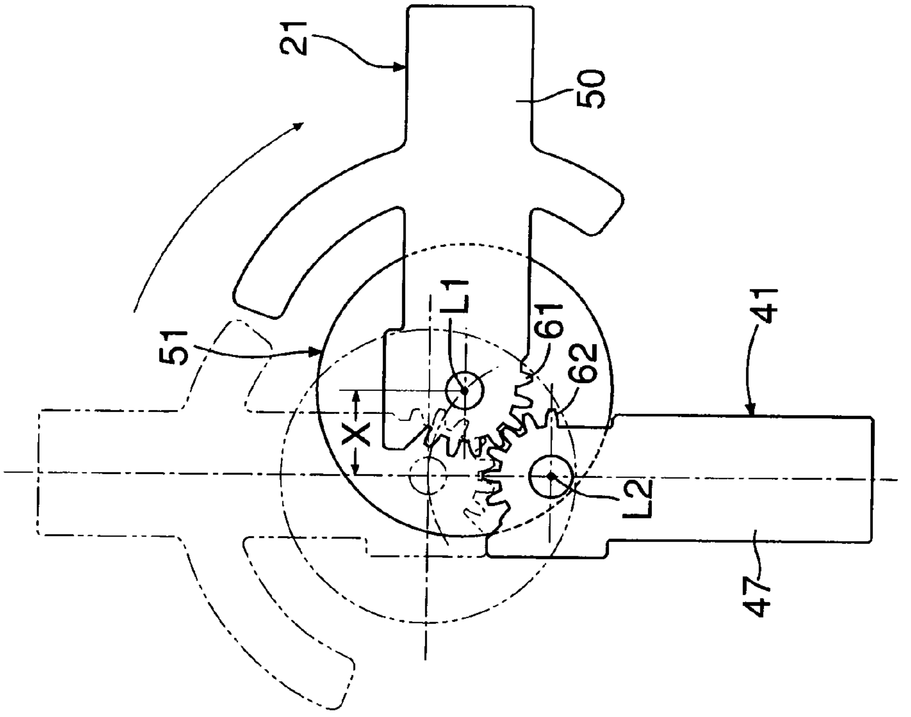
Figure 17:
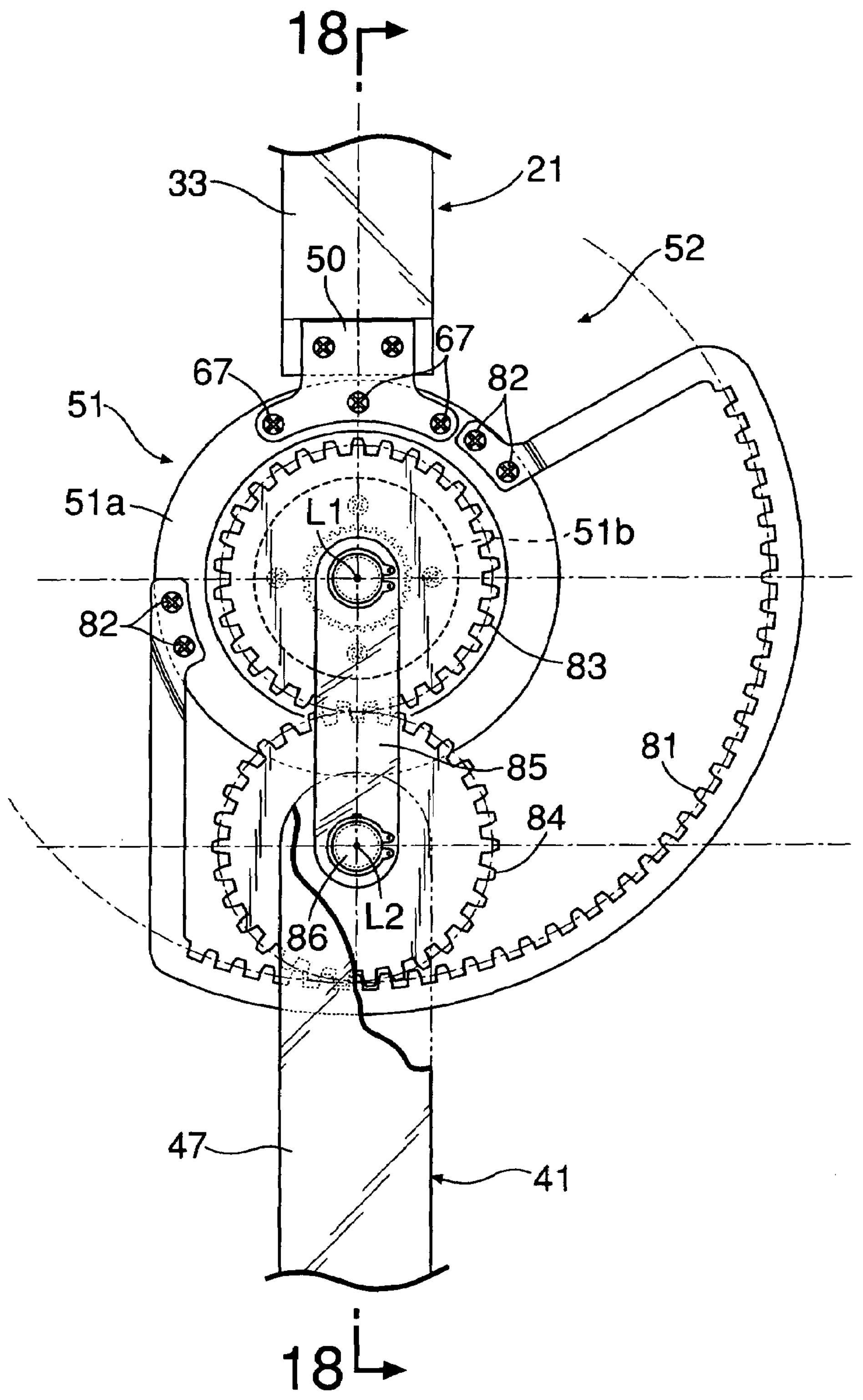
FIG. 17 is a front view of a driving force transmission mechanism.
Figure 18:
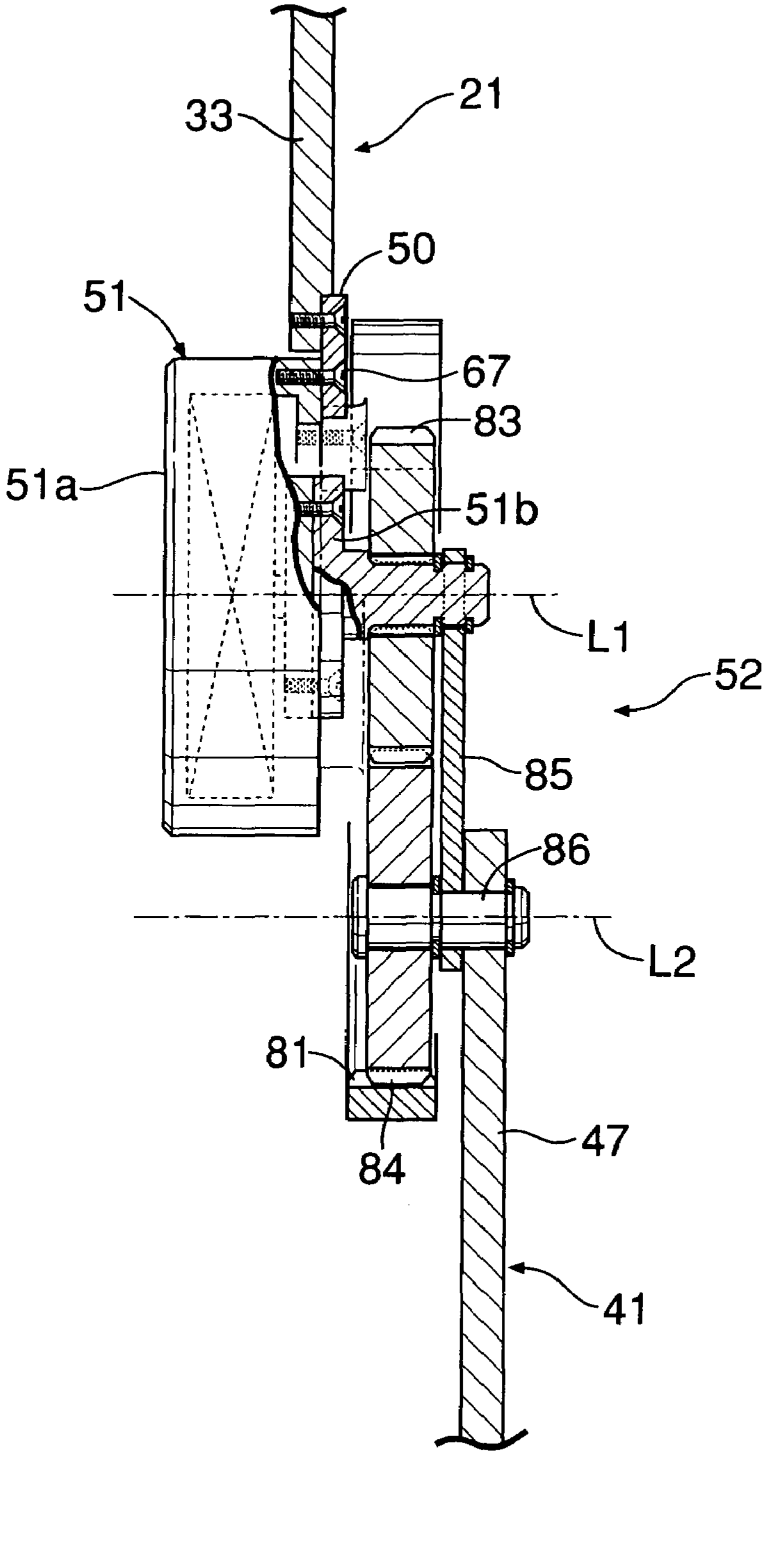
FIG. 18 is a sectional view along line 18-18 in FIG. 17.
Figure 22:
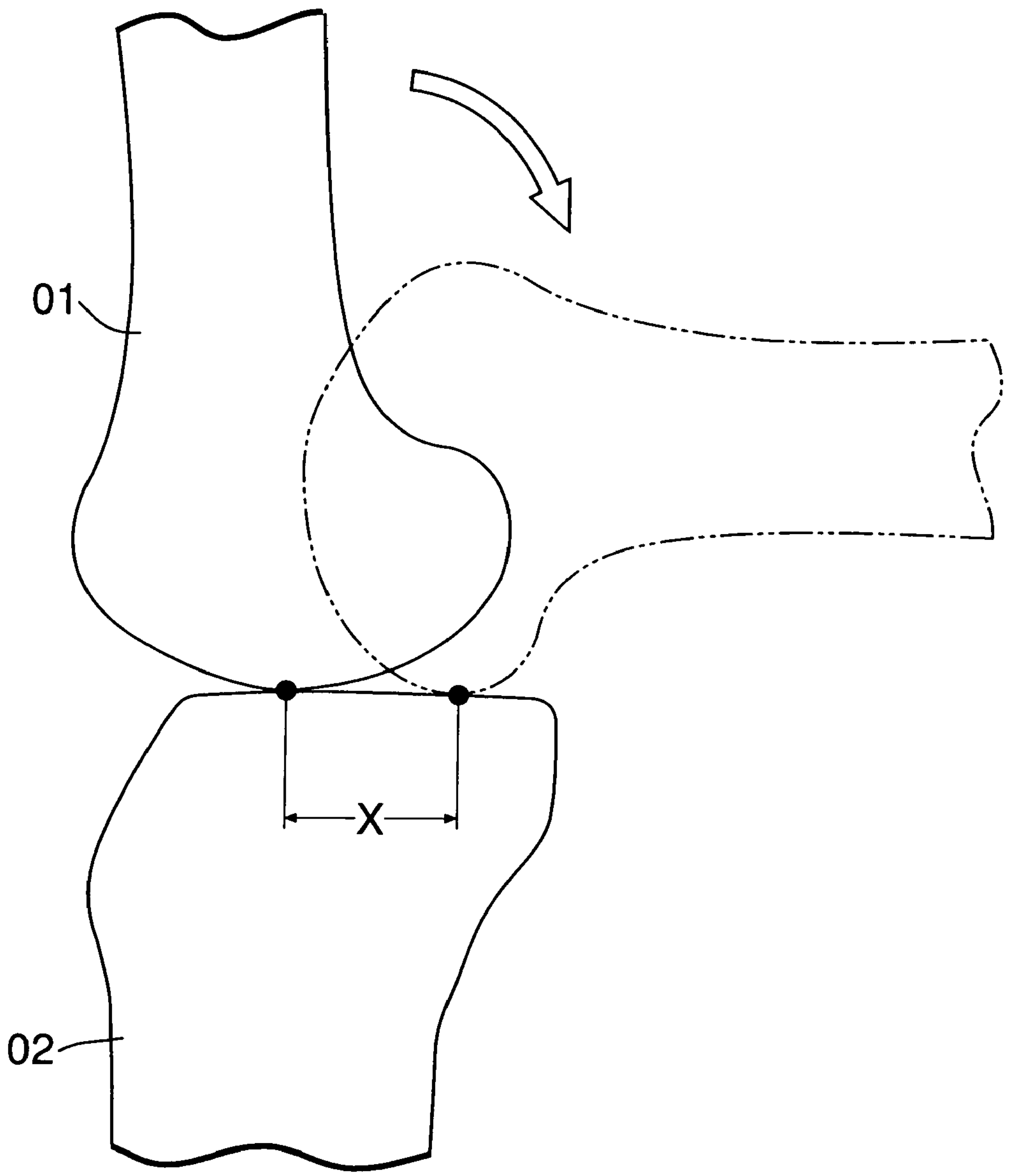
FIG. 22 is a diagram showing a state in which a thighbone is swung rearward relative to a shin bone.

When the upper leg is bent rearwardly relative to the lower leg by bending the knee joint in order to sit on a chair, the upper leg frame 21 swings rearwardly through 90° relative to the lower leg frame 41 from the broken line position to the solid line position as shown in FIG. 16B. During this process, the operation of the knee joint actuator 51 and the driving force transmission mechanism 52 are exactly the same as those of the above-mentioned case in which the lower leg is bent rearwardly relative to the upper leg. In this case, the position of the center L1 of the upper leg side gear 61 moves rearwardly by a distance X, thereby absorbing the displacement X caused when the knee joint is bent as shown in FIG. 22. This enables the upper leg fitting 12 and the lower leg fitting 13 to be prevented from rubbing against the user's skin, thus suppressing any uncomfortable sensation.

As is clear from FIG. 16A and FIG. 16B, when the knee joint actuator 51 is operated, if the rotor 51*b* rotates through 45° relative to the housing 51*a*, the upper leg frame 21 and the lower leg frame 41 rotate relative to each other through 90°. That is, the ratio of the number of revolutions of the upper leg frame 21 or the lower leg frame to the number of revolutions of the rotor 51*b* is increased by a factor of 2.

A fourth embodiment of the present invention is now described by reference to FIG. 17 to FIG. 19B.

A driving force transmission mechanism 52 of the fourth embodiment employs a planetary gear mechanism, in which a housing 51*a* of a knee joint actuator 51 is fixed to the lower end of a coupling member 33 of an upper leg frame 21 via an actuator mounting bracket 50 by bolts 67, and a ring gear 81 sharing a common axis L1 with the knee joint actuator 51 is fixed to the housing 51*a* of the knee joint actuator 51 by bolts 82. A sun gear 83 is spline-coupled to a rotor 51*b* of the knee joint actuator 51. One planetary gear 84 meshes with the ring gear 81 and the sun gear 83. Opposite ends of a planetary carrier 85 are pivotably supported by the center of the rotor 51*b* and a planetary gear shaft 86. The upper end of an output member 47 of a lower leg frame 41 is pivotably supported on the planetary gear shaft 86.

Figure 19A:
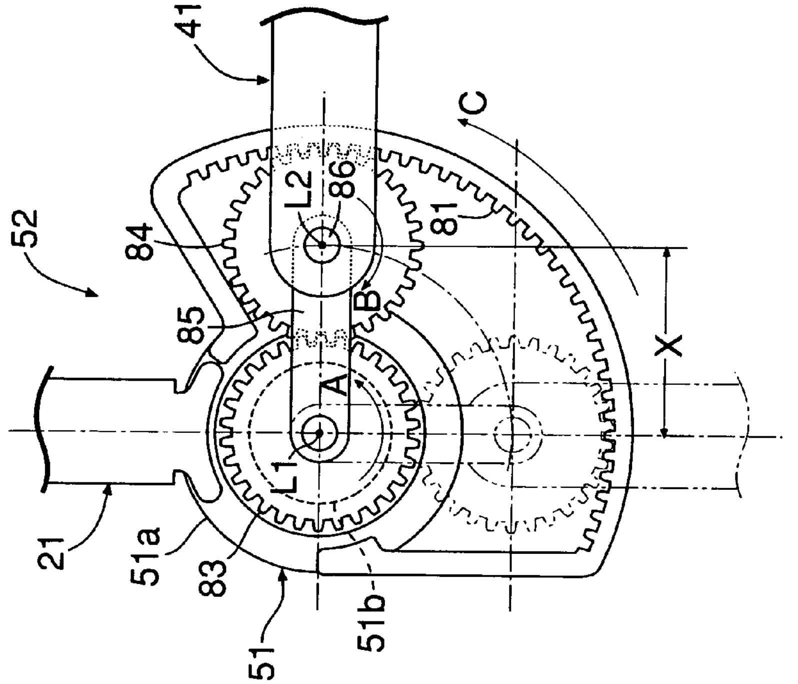
FIG. 19A and FIG. 19B are diagrams for explaining the operation.

Therefore, when a lower leg is kicked up toward the rear relative to an upper leg by bending a knee joint by means of the knee joint actuator 51 and the driving force transmission mechanism 52, if the rotor 51*b* rotates in the direction of arrow A relative to the housing 51*a* of the knee joint actuator 51 as shown in FIG. 19A, the planetary gear 84 revolves in the direction of arrow C while rotating in the direction of arrow B, and an axis L2 of the planetary gear 84 rotates through 90° with the axis L1 of the sun gear 83 as the center to move toward the rear by a distance X, thereby adsorbing the displacement X caused when the knee joint is bent as shown in FIG. 23.

During this process, although the output member 47 of the lower leg frame 41 can rotate relative to the planetary gear shaft 86, when a user is equipped with an upper leg fitting 12 and a lower leg fitting 13, since the lower leg fitting 13 is fixed to the user's lower leg, the axis L2 of the planetary gear 84, that is, the upper end of the lower leg frame 41 moves rearwardly, and the lower leg frame 41 swings rearwardly through 90° relative to the upper leg frame 21, thereby assisting the movement of the user kicking up the lower leg toward the rear.

Figure 19B:
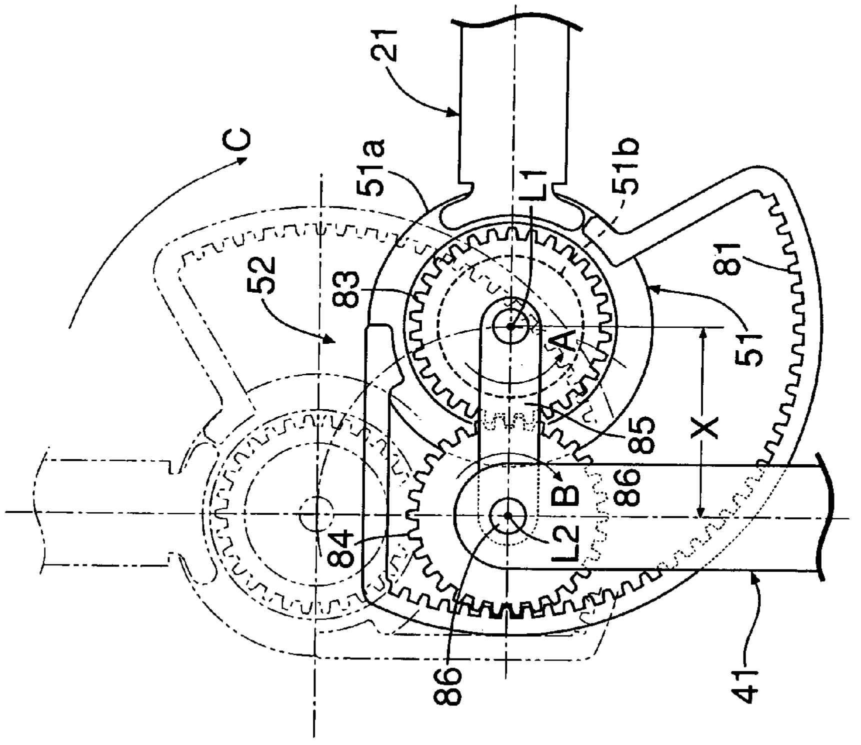

When the upper leg is bent rearwardly relative to the lower leg by bending the knee joint in order to sit on a chair, the upper leg frame 21 swings rearwardly through 90° relative to the lower leg frame 41 from the broken line position to the solid line position as shown in FIG. 19B. During this process, the operations of the knee joint actuator 51 and the driving force transmission mechanism 52 are exactly the same as those of the above-mentioned case in which the lower leg is bent rearwardly relative to the upper leg. The center L1 of the sun gear 83 moves rearwardly by a distance X relative to the center L2 of the planetary gear 84, thereby absorbing the displacement X caused when the knee joint is bent as shown in FIG. 22.

Also during this process, since the axis L1 of the sun gear 83, that is, the lower end of the upper leg frame 21, moves rearwardly, the lower leg frame 41 swings rearwardly through 90° relative to the upper leg frame 21, thereby assisting the movement of the user in bending the upper leg rearwardly.

In this embodiment, since the number of teeth of the sun gear 83 is set so as to be the same as the number of teeth of the planetary gear 84, due to the characteristics of the planetary gear mechanism, when the planetary carrier 85 rotates through 90°, the sun gear 83 rotates through 225°.

Therefore, in the fourth embodiment, the driving force transmission mechanism 52 has a reduction ratio of 2.5. Thus, it is possible to employ a knee joint actuator 51 having a small torque.

A fifth embodiment of the present invention is now described with reference to FIG. 20.

Figure 20:
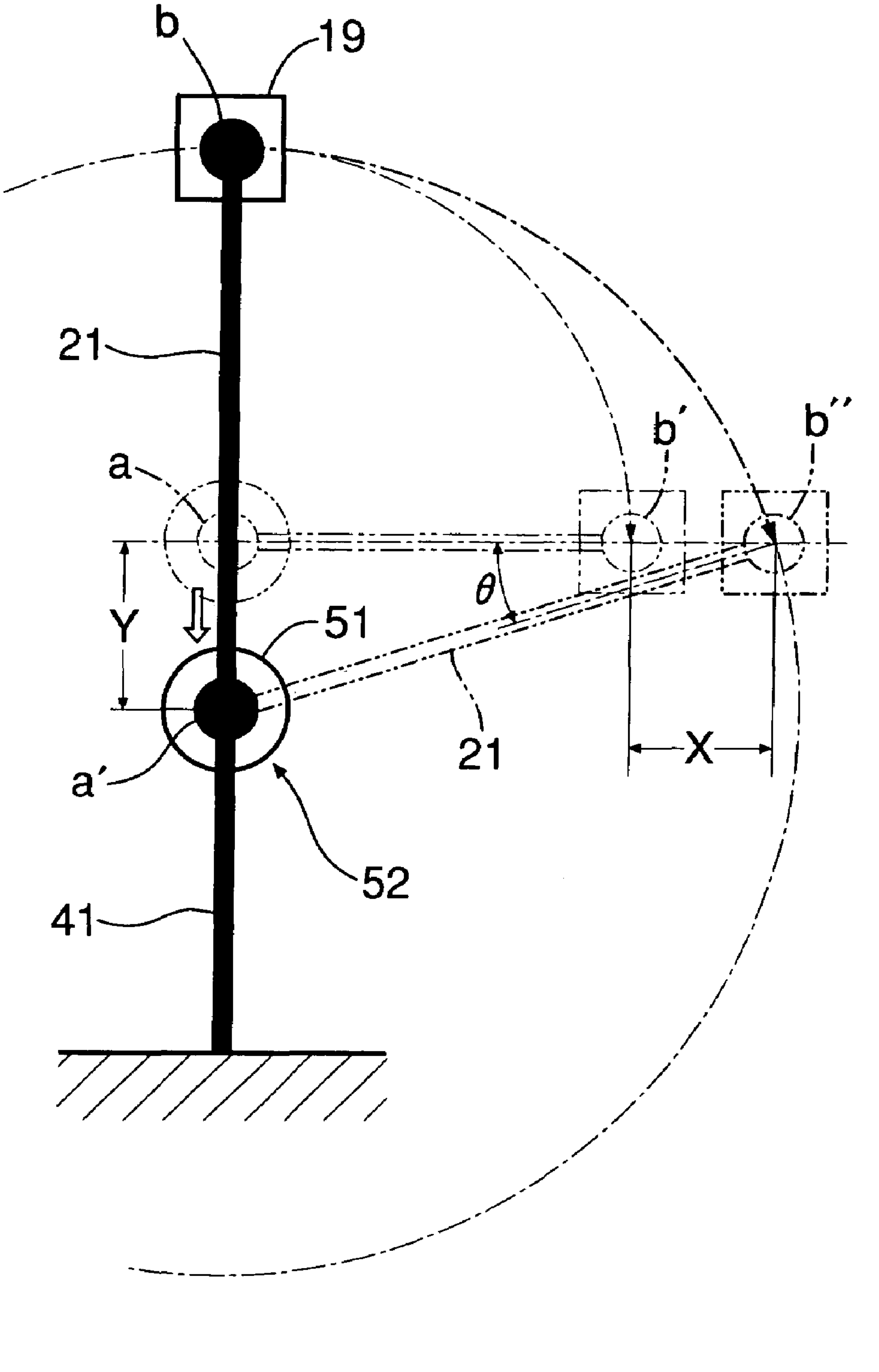
FIG. 20 is an overall side view of a walking assistance system according to an embodiment of the present invention.
Figure 21:
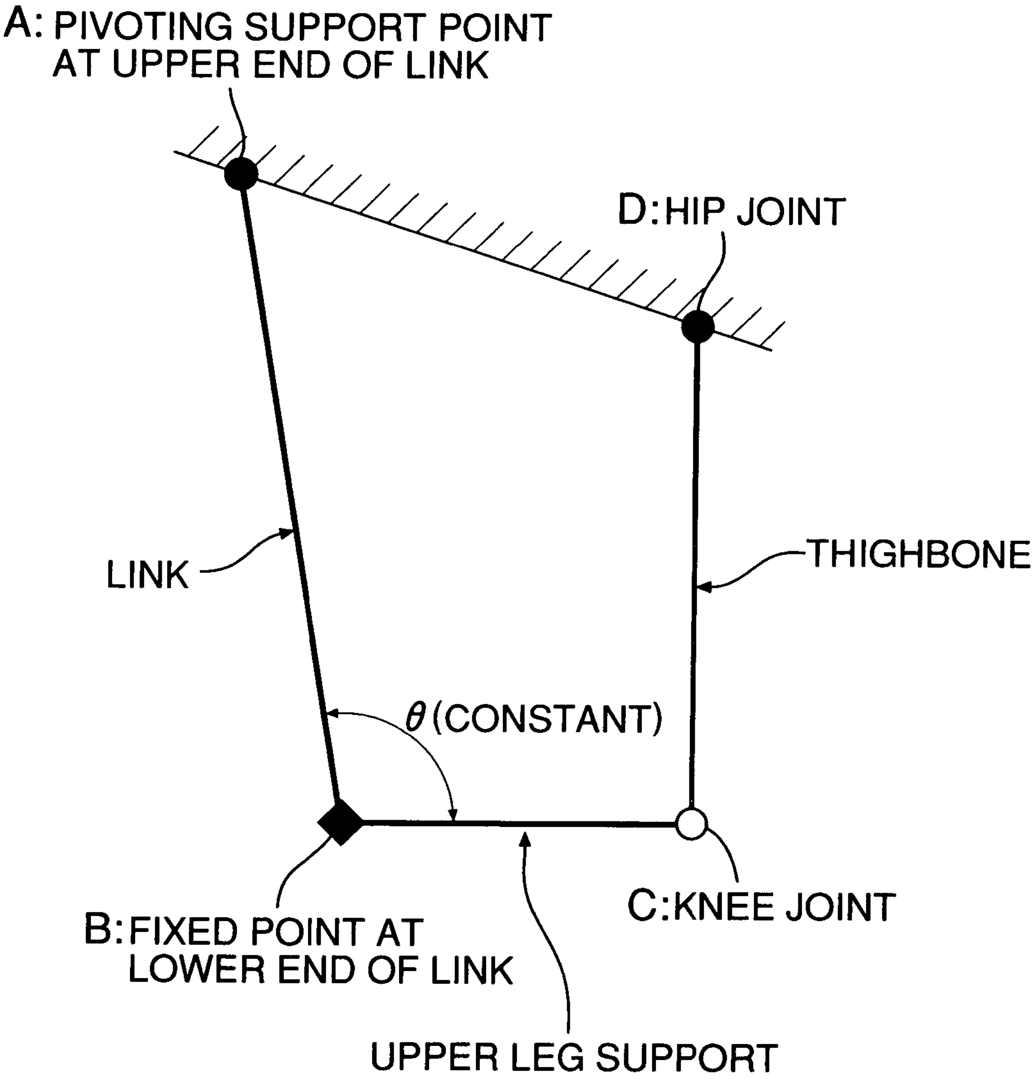
FIG. 21 is a schematic diagram showing the relationship between a hip joint and a knee joint and a fulcrum of a walking assistance system.

In FIG. 20, reference numeral a and reference numeral b denote the position of a knee joint and the position of a hip joint respectively of a standing user. When the user squats from this state, the position b of the hip joint moves to b" which is to the rear of the theoretical point b' by a distance X, due to the structure of the knee joint described by reference to FIG. 22.

In the fifth embodiment, the position of the pivoting support part between the lower end of an upper leg frame 21 and the upper end of a lower leg frame 41 (that is, the position of a knee joint actuator 51) is located at point a' which is lower than position a of the user's knee joint by a distance Y, and the upper end of the upper leg frame 21 is made swingable in the fore-and-aft direction relative to an upper leg fitting 12 by a hip joint actuator 19. A driving force transmission mechanism 52 has a simple structure, in which a housing 51*a* of the knee joint actuator 51 is only fixed to the lower end of the upper leg frame 21, and a rotor 51*b* of the knee joint actuator 51 is only fixed to the upper end of the lower leg frame 41.

Thus, by driving the knee joint actuator 51 so as to swing the upper leg frame 21 rearwardly around point a' relative to the lower leg frame 41, the position of the hip joint moves from b to b", thereby absorbing the distance X which is the amount of displacement due to the structure of the knee joint. During this process, although it is necessary for the upper leg frame 21 to swing through an angle θ relative to the upper leg fitting 12, this angle θ can be easily generated by control of the hip joint actuator 19.

Although embodiments of the present invention have been described above, the present invention is not limited to the above-mentioned embodiments, and can be modified in a variety of ways without departing from the subject matter of the present invention described in the claims.

For example, the walking assistance systems of the embodiments are described as an assistance for walking, but they may be used in order to increase leg power when a user lifts heavy items.

Further, the adjustment actuator of the present invention is not limited to the hydraulic cylinder 73 of the embodiment, and may employ another structure such as a ball screw mechanism.

Furthermore, in the fourth embodiment, the upper end of the lower leg frame 41 is pivotably supported on the planetary carrier 85 at the center L2 of the planetary gear 84, but the upper end of the lower leg frame 41 may be pivotably supported at any position of the planetary carrier 85.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A walking assistance system comprising:

an upper leg fitting adapted to be attached along a user's upper leg;

a lower leg fitting adapted to be attached along the user's lower leg;

a hip joint actuator adapted to be disposed to one side of the user's hip joint in order to make the upper leg fitting swing in the fore-and-aft direction relative to the user's hip; and a knee joint actuator disposed to one side of the user's knee joint in order to make the lower leg fitting swing in the fore-and-aft direction relative to the upper leg fitting;

the upper leg fitting comprising an upper leg frame forming a framework of the upper leg fitting, and an upper leg coupling member provided on the upper leg frame and joined to the upper leg; and the upper leg coupling member being relatively movably supported on the upper leg frame, wherein the upper leg coupling member is supported so that it can slide alone the longitudinal direction of the upper leg frame and can rotate around a support shaft extending in the left-and-right direction relative to the upper leg frame.

2. The walking assistance system according to claim 1, wherein the upper leg coupling member is formed from a first arm part fixed to an upper part of the rotating member by bolts so as to face upward, a U-shaped first upper leg coupling part fixed to the upper end of the first arm part and resiliently engaging with the user's upper leg, a second arm part fixed to a lower part of the rotating member by other bolts so as to face downward, and a U-shaped second upper leg coupling part fixed to a lower end of the second arm part and resiliently engaging with the user's upper leg.

3. A walking assistance system comprising:

an upper leg fitting adapted to be attached along a user's upper leg;

a lower leg fitting adapted to be attached along the user's lower leg;

a hip joint actuator disposed to one side of the user's hip joint in order to make the upper leg fitting swing in the fore-and-aft direction relative to the user's hip; and a knee joint actuator disposed to one side of the knee joint in order to make the lower leg fitting swing in the fore-and-aft direction relative to the upper leg fitting;

an upper end of an upper leg frame that forms a framework of the upper leg fitting being pivotably supported so that it can swing in the left-and-right direction relative to the hip joint actuator around an upper fulcrum pin; and the lower end of the upper leg frame being pivotably supported so that it can swing in the left-and-fight direction relative to the knee joint actuator around a lower fulcrum pin.

4. The walking assistance system according to claim 3, wherein the length of the upper leg frame is adjustable by an expandable adjustment actuator.

5. The walking assistance system according to claim 4, wherein the adjustment actuator has a damper function for damping expansion and contraction of the upper leg frame.

6. The walking assistance system according to claim 3, wherein the upper leg frame includes a lower frame which is a pipe having a rectangular cross-section and an upper frame slidably fitted into an upper end of the lower frame.

7. The walking assistance system according to claim 6, wherein opposite ends of the adjustment actuator are connected by pins to a pair of brackets that project on side faces of the lower frame and the upper frame.

8. A walking assistance system comprising:

an upper leg fitting adapted to be attached along a user's upper leg;

a lower leg fitting adapted to be attached along the user's lower leg; and a knee joint actuator disposed to one side of the user's knee joint in order to make the upper leg fitting and the lower leg fitting swing relative to each other in the fore-and-aft direction;

a housing of the knee joint actuator, which is fixed to the lower end of an upper leg frame forming a framework of the upper leg fitting;

a rotor of the knee joint actuator, which is coupled via a driving force transmission mechanism to the upper end of a lower leg frame forming a framework of the lower leg fitting; and the driving force transmission mechanism making the lower end of the upper leg frame and the upper end of the lower leg frame move relative to each other in the fore-and-aft direction so as to follow relative movement in the fore-and-aft direction between the lower end of the upper leg and the upper end of the lower leg accompanying bending or stretching of the knee joint.

9. The walking assistance system according to claim 8, wherein the driving force transmission mechanism comprises an upper leg side gear fixed to the lower end of the upper leg frame, and a lower leg side gear fixed to the upper end of the lower leg frame and meshing with the upper leg side gear, and wherein the rotor of the knee joint actuator drives the lower leg side gear so that the lower leg side gear revolves around the upper leg side gear while rotating.

10. The walking assistance system according to claim 8, wherein the driving force transmission mechanism is a planetary gear mechanism comprising: a ring gear fixed to the lower end of the upper leg frame; a sun gear that is fixed to the rotor of the knee joint actuator and that shares a common center with the ring gear; a planetary gear meshing with the sun gear and the ring gear; and a planetary carrier that supports the planetary gear so that it can rotate around the sun gear, for pivotably supporting the upper end of the lower leg frame.

11. The walking assistance system according to claim 8, wherein the driving force transmission mechanism is established by fixing the rotor of the knee joint actuator to the upper end of the lower leg frame, wherein a rotating shaft of the rotor of the knee joint actuator is positioned lower than the knee joint, and wherein the upper end of an upper frame is pivotably supported on the upper leg fitting.

* * * * *